United States Patent
Kaifu et al.

[11] Patent Number: 5,935,756
[45] Date of Patent: Aug. 10, 1999

[54] DIAZONIUM SALT FOR THERMOSENSITIVE RECORDING MEDIUM

[75] Inventors: Katsuaki Kaifu; Akihiko Nishiki; Takeshi Koyano, all of Tokyo, Japan

[73] Assignee: Oki Electric Industry Co., Ltd., Tokyo, Japan

[21] Appl. No.: 08/876,512

[22] Filed: Jun. 16, 1997

[30] Foreign Application Priority Data

Jul. 4, 1996 [JP] Japan ..................................... 8-175038
Feb. 14, 1997 [JP] Japan ..................................... 9-030839

[51] Int. Cl.⁶ .............................. G03F 7/016; G03C 1/54; C07C 245/20
[52] U.S. Cl. .......................... 430/138; 430/157; 430/163; 430/171; 534/558
[58] Field of Search ..................... 430/138, 171, 430/157, 162, 176, 177, 163; 534/558

[56] References Cited

U.S. PATENT DOCUMENTS

| | | | |
|---|---|---|---|
| 4,590,263 | 5/1986 | Desjarlais et al. | 430/157 |
| 4,760,048 | 7/1988 | Kurihara et al. | 430/171 |
| 4,771,032 | 9/1988 | Yamaguchi et al. | 430/151 |
| 4,965,166 | 10/1990 | Hosoi et al. | 430/151 |
| 4,980,260 | 12/1990 | Shinozaki et al. | 430/171 |
| 5,776,652 | 7/1998 | Eichhorn et al. | 430/163 |

FOREIGN PATENT DOCUMENTS

| | | |
|---|---|---|
| 0 269 440 | 6/1988 | European Pat. Off. . |
| 9-109559 | 4/1997 | Japan . |
| 1 378 861 | 12/1974 | United Kingdom . |
| 2 164 166 | 3/1986 | United Kingdom . |

*Primary Examiner*—John S. Chu
*Attorney, Agent, or Firm*—Venable; Robert J. Frank; Ashley J. Wells

[57] ABSTRACT

A diazonium salt for a color-forming layer of a thermosensitive recording medium, having formula (1):

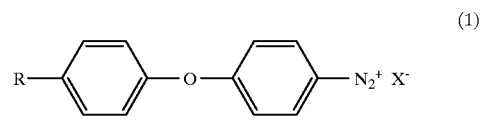

(1)

wherein R is an alkyl group having four carbon atoms which is selected from the group consisting of n-butyl, t-butyl, and sec-butyl, and $X^-$ is selected from the group consisting of hexafluorophosphate ion $PF_6^-$, tetrafluoroborate ion $BF_4^-$ and tetraphenylborate ion $(C_6H_5)_4 B^-$. In a first embodiment, a thermosensitive recording medium has a color-forming layer which includes a diazonium salt as described above, a basic compound and a coupler. In a second embodiment, a thermosensitive recording medium has a color-forming layer which includes: a diazonium salt, a basic compound, and a coupler, wherein the diazonium salt has a formula (2):

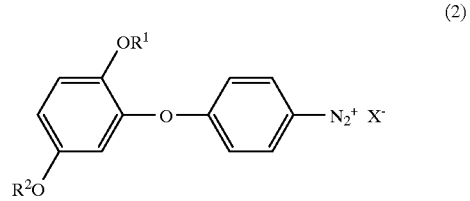

(2)

where $R^1$ and $R^2$ are alkyl groups each having one or more carbon atoms, and $X^-$ is selected from the group consisting of hexafluorophosphate ion $PF_6^-$, tetrafluoroborate ion $BF_4^-$ and tetraphenylborate ion $(C_6H_5)_4B^-$.

8 Claims, 3 Drawing Sheets

DIAZONIUM SALT FOR THERMOSENSITIVE RECORDING MEDIUM

BACKGROUND OF THE INVENTION

1. Field of the Invention

The present invention relates to a diazonium salt used for a color-forming layer of a thermosensitive recording medium. More particularly, it relates to a diazonium salt which develops a red or yellow color when it reacts with a coupler, dissolves to a high concentration in capsule oil when sealed together with capsule oil in a microcapsule, and provides a thermosensitive recording medium that forms a high density, high contrast thermosensitive image and can prevent forgeries.

2. Description of the Related Art

In recent years, a thermosensitive recording medium using a diazonium salt which undergoes photodecomposition is replacing conventional thermosensitive recording media using color-forming leucodyes. The thermosensitive recording medium has a color-forming layer including a diazonium salt, coupler and basic compound on a support. It is known that, to improve the keeping properties of the thermosensitive recording medium, the diazonium salt is sealed together with capsule oil in a microcapsule by interface polymerization and is separated by the microcapsule wall from the coupler and basic compound so that it does not develop a color before exposing to heat. The thermosensitive recording medium using a diazonium salt is disclosed, for example, "Microcapsules" by Tamotsu Kondo, pp. 65–75, ed. Japan Standards Association (1991).

However, while many thermosensitive recording media using diazonium salts are known which develop a blue color, hardly any are known which develop a red or yellow color. In other words, although it also depends on the coupler, there are many diazonium salts which develop a blue color when they react with a coupler, and very few which develop a red or yellow color.

When the diazonium salt is sealed in the microcapsule, the diazonium salt must be dissolved in an oil (referred to hereafter as capsule oil) which forms the core of the capsule in order to form a stable emulsion which has a uniform particle diameter.

However, conventional diazonium salts have a low solubility in capsule oils such as dibutyl phthalate or tricresyl phosphate. For example, 4-diazodiphenyletherhexafluorophosphate, which is generally used for developing a red color, has a solubility of 0.5 [g] or less in 100 [g] of dibutyl phthalate or 100 [g] of tricresyl phosphate. Further, even 4-diazo-4'-methyldiphenyletherhexafluorophosphate, which is generally said to have a high solubility in capsule oil, has a solubility of 1.0 [g] or less in 100 [g] of dibutyl phthalate or 100 [g] of tricresyl phosphate.

A method was therefore proposed for adding a polar solvent such as acetone to raise the solubility of a diazonium salt such as 4-diazodiphenyletherhexafluorophosphate or 4-diazo-4'-methyldiphenyletherhexafluorophosphate in capsule oil in Japanese Patent Application No. 36215/1996.

However, as the polar solvent is also highly soluble in water, when the capsule oil, in which the diazonium salt is dissolved, is dispersed in water giving an aqueous emulsion, the diazonium salt tended to move into the aqueous phase and precipitated so that a concentration of the diazonium salt in the microcapsule fell. It is therefore necessary to dissolve a high concentration of the diazonium salt in the capsule oil alone without adding a polar solvent.

Hence, a diazonium salt, which is sealed together with capsule oil in a microcapsule and used for a color-forming layer of the thermosensitive recording media, was desired having the following properties:

[1] Develops a red or yellow color when it reacts with a coupler,

[2] Has a high solubility in capsule oil, specifically a solubility of 1 [g] or higher and preferably of 3–30 [g] per 100 [g] of capsule oil, and is capable of forming a high density, high contrast image, and

[3] provides a thermosensitive recording medium which can prevent forgeries.

In general, conventional diazonium salts are costly, and as they have poor thermal stability, their use in thermosensitive recording media was limited. A less expensive diazonium salt which had good heat withstanding properties was therefore required.

SUMMARY OF THE INVENTION

It is an object of the present invention to provide a diazonium salt for a color-forming layer of a thermosensitive recording medium, which develops a red or yellow color when it reacts with the coupler, and dissolves to a high concentration in capsule oil when sealed together with capsule oil in a microcapsule.

It is another object of the present invention to provide a thermosensitive recording medium which has a color-forming layer including a diazonium salt, can form a high density, high contrast thermosensitive image and can prevent forgeries.

According to one aspect of the present invention, a diazonium salt for a color-forming layer of a thermosensitive recording medium, having the formula (1):

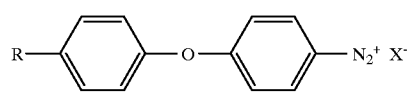

(1)

wherein R is an alkyl group having two or more carbon atoms, and $X^-$ is selected from the group consisting of hexafluorophosphate ion $PF_6^-$, tetrafluoroborate ion $BF_4^-$ and tetraphenylborate ion $(C_6H_5)_4B^-$.

According to another aspect of the present invention, a diazonium salt for a color-forming layer of a thermosensitive recording medium, having the formula (2):

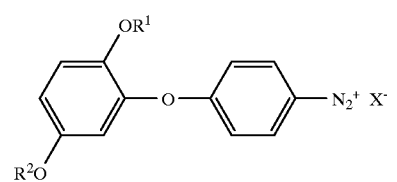

(2)

wherein $R^1$ and $R^2$ are alkyl groups each having one or more carbon atoms, and $X^-$ is selected from the group consisting of hexafluorophosphate ion $PF_6^-$, tetrafluoroborate ion $BF_4^-$ and tetraphenylborate ion $(C_6H_5)_4B^-$.

According to still another aspect of the present invention, a thermosensitive recording medium comprising a color-forming layer which includes a diazonium salt, a basic compound and a coupler: the diazonium salt having the formula (1):

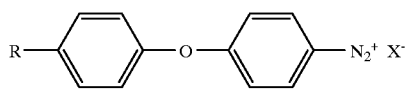

(1)

wherein R is an alkyl group having two or more carbon atoms, and X⁻ is selected from the group consisting of hexafluorophosphate ion $PF_6^-$, tetrafluoroborate ion $BF_4^-$ and tetraphenylborate ion $(C_6H_5)_4B^-$.

According to further aspect of the present invention, a thermosensitive recording medium comprising a color-forming layer which includes a diazonium salt, a basic compound and a coupler: the diazonium salt having the formula (2):

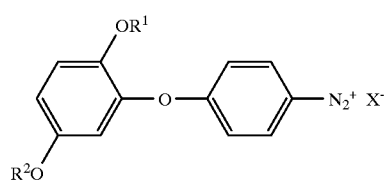

(2)

wherein $R^1$ and $R^2$ are alkyl groups each having one or more carbon atoms, and X⁻ is selected from the group consisting of hexafluorophosphate ion $PF_6^-$, tetrafluoroborate ion $BF_4^-$ and tetraphenylborate ion $(C_6H_5)_4B^-$.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
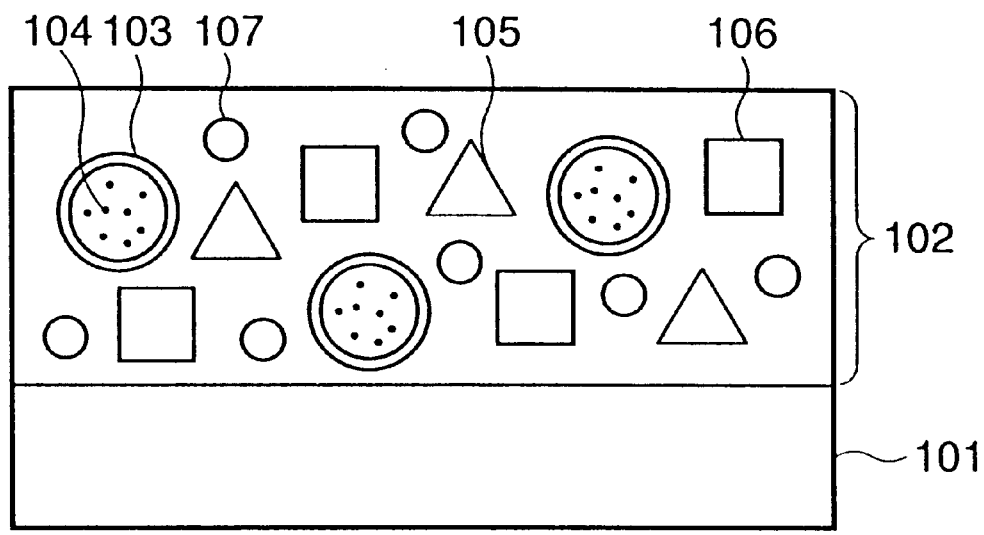
FIG. 1 is a sectional view conceptually showing a thermosensitive recording paper having a film-forming layer according to the present invention.

Further scope of applicability of the present invention will become apparent from the detailed description given hereinafter. However, it should be understood that the detailed description and specific examples, while indicating preferred embodiments of the invention, are given by way of illustration only, since various changes and information will become apparent to those skilled in the art from the detailed description.

A color-forming layer of a thermosensitive recording medium includes a diazonium salt, a basic compound and a coupler.

An example of the diazonium salt (referred to hereinafter as a first diazonium salt) for a color-forming layer of a thermosensitive recording medium according to the present invention is represented by the following formula (1):

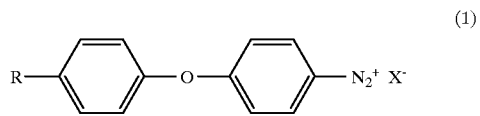

(1)

wherein R is an alkyl group having two or more carbon atoms, and X⁻ is selected from the group consisting of hexafluorophosphate ion $PF_6^-$, tetrafluoroborate ion $BF_4^-$ and tetraphenylborate ion $(C_6H_5)_4B^-$.

Further, another example of the diazonium salt (referred to hereafter as a second diazonium salt) for a thermosensitive recording medium according to the present invention is represented by the following formula (2):

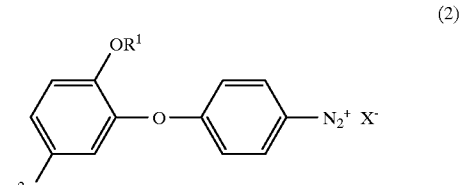

(2)

wherein $R^1$ and $R^2$ are alkyl groups each having one or more carbon atoms, $R^1$ and $R^2$ may be the same or different, and X⁻ is selected from the group consisting of hexafluorophosphate ion $PF_6^-$, tetrafluoroborate ion $BF_4^-$ and tetraphenylborate $(C_6H_5)_4B^-$ ion.

R in the first diazonium salt represented by the above formula (1), and $R^1$ and $R^2$ in the second diazonium salt represented by the above formula (2), may be alkyl groups with 3–8 carbon atoms. This is because when there are 3 or more carbon atoms, the diazonium salt can be dissolved to a high concentration in capsule oil. Moreover, in the case of an alkyl group with 8 or less carbon atoms, the diazonium chloride formed in a diazotization step when the diazonium salt is synthesized, which is described in detail with regard to a later process, is soluble in water so that a hexafluorophosphate salt, tetrafluoroborate salt or tetraphenylborate salt is easily prepared.

Therefore, the alkyl group R in the first diazonium salt represented by the above formula (1) and the alkyl groups $R^1$ and $R^2$ in the second diazonium salt represented by the above formula (2) may, for example, be propyl, butyl, pentyl (i.e., amyl), hexyl, heptyl or octyl, in addition to which cycloalkyl, alkyl halide or the like are also suitable.

Butyl is particularly suitable as the alkyl group R of the first diazonium salt represented by the above formula (1) as it confers high solubility in capsule oil. Further, t-butyl and sec-butyl are especially suitable for the purpose of the present invention as these functional groups can be easily introduced using low-cost starting materials and the thermal stability of the resulting compounds is 115° C. or higher (i.e., thermal decontamination temperature is 115° C. or higher).

The first or second diazonium salt of the present invention reacts with a coupler which is a hydroxynaphthoic acid derivative such as naphthol AS, naphthol AS-D, naphthol AS-OL, naphthol AS-PH, naphthol AS-MX, naphthol AS-BO, naphthol AS-BS or naphthol AS-SW, so as to develop a red color or a magenta color.

Likewise, the first or second diazonium salt of the present invention reacts with a coupler which is an acetoacetic acid derivative such as naphthol AS-G, naphthol AS-LG, naphthol AS-L3G or naphthol AS-L4G so as to develop a yellow color.

Therefore, by mixing naphthol AS and naphthol AS-G in a suitable proportion to use naphthol AS and naphthol AS-G as the coupler, and reacting the mixture with the first or second diazonium salt according to the present invention, an orange color, red color, pink color or the like may also be developed.

Next, the capsule oil in which the first or second diazonium salt of the present invention are dissolved will be described. This capsule oil dissolves a predetermined amount of diazonium salt, and forms a homogenous, stable emulsion in water. Ultimately, it has the important role of forming capsules of uniform particle diameter at the emulsion interface by interface polymerization.

Specific examples of capsule oil are phthalic acid esters such as dibutyl phthalate and dioctyl phthalate, or phosphoric acid esters such as tricresyl phosphate, tributyl phosphate and triphenyl phosphate. These oils are most suitable as they have predetermined polar groups, form a homogenous, stable emulsion, and have a boiling point of 250° C. or higher, consequently they exhibit stability to the heat of a thermal head when used on thermosensitive paper.

The first and second diazonium salts of the present invention are, for example, characterized in that they have a high solubility in capsule oils such as dibutyl phthalate and tricresyl phosphate. Specifically, the diazonium salts of the present invention exhibit a solubility of 1 [g] or higher in 100 [g] of these capsule oils. Hence, when the diazonium salts of the present invention having this solubility range are used in thermosensitive recording media, it is possible to give a high density, high contrast print.

It is therefore more preferable that the diazonium salt of the present invention has a solubility in the range 1–50 [g], and still more preferably 3–30 [g], with respect to 100 [g] of capsule oil. This is due to the fact that within these solubility limits, a print of still higher density and contrast can be obtained.

For example, 4-diazo-4'-n-butyldiphenyletherhexafluorophosphate, the first diazonium salt, has a solubility of 8 [g] in 100 [g] of dibutyl phthalate and 12 [g] in 100 [g] of tricresyl phosphate. Likewise, 4-diazo-4'-t-butyldiphenyletherhexafluorophosphate has a solubility of 8 [g] in 100 [g] of dibutyl phthalate, and 8 [g] in 100 [g] of tricresyl phosphate. Further, 4-diazo-4'-sec-butyldiphenyletherhexafluorophosphate has a solubility of 8 [g] in 100 [g] of dibutyl phthalate, 8 [g] in 100 [g] of tricresyl phosphate, and 10 [g] or more in 100 [g] of tricresyl phosphate. These compounds are therefore suitable as the diazonium salts of the present invention.

Likewise, 4-diazo-2',5'-di-n-butoxydiphenyletherhexafluorophosphate has a solubility of 20 [g] or more in either 100 [g] of dibutyl phthalate or 100 [g] of tricresyl phosphate, and is therefore suitable for the purpose of the present invention.

Next, the basic compound used in conjunction with the diazonium salt of the present invention will be described. In the thermosensitive recording medium in which the diazonium salt of the present invention is used, a predetermined amount of the basic compound is added to establish basic conditions so that the diazonium salt and coupler react together, thereby developing a color.

Specific examples of basic compounds which may be suitably used are organoammonium salts, organoamines, amide compounds, urea derivatives, thiourea derivatives, thiazoles, pyrroles, pyrimidines, piperazines, guanidines, indoles, imidazoles, imidazolines, triazoles, morpholines, piperizines, amidines, pyridines or the like.

More specifically, tricyclohexylamine, tribenzylamine, octadecylbenzylamine, stearylamine, allyl urea, thiourea, methylthiourea, allyl thiourea, ethylene thiourea, 2-benzylimidazoles, 4-phenylimidazoles, 2-phenyl-4-methylimidazoles, 2-undecylimidazolines, 2,4,5-trifuryl-2-imidazoline, 1,2,3-triphenylguanidines, 1,2-dicyclohexylguanidines,1,2,3-tricyclohexylguanidine, guanidine trichloroacetate, N,N'-dibenzylpiperazine, 4-4'-dithiomorpholine, morpholinium trichloroacetate, 2-aminobenzothiazole, and 2-benzoylhydrazinobenzothiazole are suitable as the basic compound of the present invention.

There is no particular limitation on the addition amount of this basic compound, however an addition in the range 1–5000 weight parts per 100 weight parts of diazonium salt is suitable. This is because when the addition of basic compound is within this range, a predetermined addition effect is obtained, and a high density, high contrast image can be formed without decreasing the relative amounts of diazonium salts and coupler.

However, to improve balance, a more suitable addition amount of basic compound is 10–1000 weight parts per 100 weight parts of diazonium salt, the optimum addition amount being in the range 100–400 weight parts.

Next, a description will be given of a sensitizer used in conjunction with the diazonium salt of the present invention in the same way as the basic compound. In a thermosensitive recording medium in which the diazonium salt of the present invention is used, the sensitizer melts on exposure to heat, the viscosity of the color-forming layer as a whole decreases, and the reaction between the diazonium salt and coupler proceeds more efficiently.

This sensitizer may be insoluble in water, and when it has a comparatively low molecular weight (average molecular weight less than 10,000, or preferably 1,000), it is easily melted by the action of heat and has good compatibility with the diazonium salt and coupler. Specific examples of the sensitizer are hydroxybenzoic acid derivatives, fatty acid amides, zinc stearates, α-naphthylbenzylether, β-naphthylbenzylether, β-naphthoic acid phenyl ester, α-hydroxy-β-naphthoic acid phenyl ester, β-naphthol-(p-chlorobenzyl)ether, 1,4-butadiol-p-methylphenylether, 1,4-butadiol-p-ethylphenylether, 1,4-butadiol-m-methylphenylether, 1,4-phenoxy-2-(p-chlorophenoxy) ethane and p-benzylphenyl. These compounds have a high sensitizing action together with a high heat resistance, and are therefore suitable for the purpose of the present invention.

There is no particular limitation on the addition amount of this sensitizer, however an addition in the range 1–1000 weight parts per 100 weight parts of diazonium salt is suitable. This is because when the addition of basic compound is within this range, a predetermined addition effect is obtained, and a high density, high contrast image can be formed without decreasing the relative amounts of diazonium salts and coupler.

However, to improve balance, a more suitable addition amount of sensitizer is 10–1000 weight parts per 100 weight parts of diazonium salt, the optimum addition amount being in the range 400–800 weight parts.

Next, the heat resistance of the diazonium salt of the present invention will be described. To improve the keeping properties of the thermosensitive recording medium for long periods so that no color develops before exposure to heat, it is desirable that the diazonium salt of the present invention has a predetermined heat resistance. It is therefore desirable that the diazonium salt has a predetermined thermal decomposition temperature, measured as a melting peak temperature by a DTA (differential thermal analyzer).

Specifically, it is desirable that, defining the thermal decomposition temperature as an exothermic peak temperature due to thermal decomposition, this temperature is 70° C. or higher when, for example, a 10 [mg] sample of the diazonium salt is heated in air at a rate of 10° C./min using the DTA to increase the temperature. This is because, if the diazonium salt of the present invention has a thermal decomposition temperature within this range, the thermosensitive recording medium can be kept over comparatively long periods before exposure to heat.

A more suitable thermal decomposition temperature of the diazonium salt is within the range 90–180° C., and preferably 115–160° C. This is because, if the diazonium salt of the present invention has a thermal decomposition temperature within this range, the thermosensitive recording medium can be kept over still longer periods before exposure to heat, and when it is exposed to heat, a high density, high contrast image can be formed at comparatively low temperature.

Next, the method of using the diazonium salt of the present invention in a thermosensitive recording medium will be described. A method of manufacturing a thermosensitive recording medium using this diazonium salt will also be described, but it should be understood that a use of the diazonium salt according to the present invention is not limited to this manufacturing method.

[1] First, a mixed solution is prepared from the diazonium salt of the present invention, a predetermined amount of capsule oil and an isocyanate compound. After blending with an aqueous solution of polyvinyl alcohol made up separately, water is added so that an emulsion is made by aqueous emulsification.

[2] More water is then added to fully react with the isocyanate compound, which is a capsule wall material, so as to give microcapsules of a predetermined particle diameter in which the diazonium salt of the present invention and capsule oil are sealed.

[3] The microcapsules thus obtained are mixed with a predetermined amount of coupler, basic compound and sensitizer so as to give a homogeneous stirred solution.

[4] This stirred solution is coated to a predetermined thickness on a paper or other substrate, and dried so as to give a thermosensitive recording medium using the diazonium salt of the present invention.

In FIG. 1, a numeral 101 is the paper, 102 is a color-forming layer, 103 is the microcapsule, 104 is the diazonium salt, 105 is the coupler, 106 is the basic compound, and 107 is the sensitizer.

When this thermosensitive recording medium is heated to form a predetermined image using a thermal head, the sensitizer 107 first melts, thereby lowering the viscosity of the whole medium so that the coupler 105, basic compound 106 and the diazonium salt 104 of the present invention mix easily together. The mixed coupler 105 and diazonium salt 104 then react in the basic environment, and a red or yellow color is developed.

When it is not desired to form an image by further heating, to prevent forgery, it is desirable to decompose the diazonium salt which is not colored without heating by exposing it to ultraviolet light of wavelength 250–380 [nm] using an ultraviolet light irradiating device. When this is done, the diazonium salt can no longer react with the coupler to develop a color even if it is heated again.

The reason why the ultraviolet light wavelength range is 250–380 [nm], is that ultraviolet light of this wavelength efficiently decomposes unreacted diazonium salt alone, and it is also comparatively safe.

Next, some preferred embodiments of the present invention will now be described with reference to the accompanying drawings. It will of course be understood that in the following description the materials used, numerical conditions such as quantities, treatment temperatures and treatment times, and treatment methods, are given only as examples and not to be construed as limiting the scope of the present invention in any way.

First Embodiment

The diazonium salt of the first embodiment, represented by the following general formula (3), is 4-diazo-4'-n-butyldiphenyletherhexafluorophosphate in which R is the n-butyl group, $(CH_3(CH_2)_3{}^-)$.

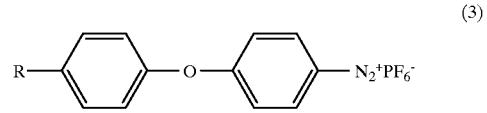

(3)

Next, a method of synthesizing the diazonium salt of this embodiment will be described.

[1] Synthesis of 4-nitro-4'-n-butyldiphenylether

First, 4-nitro-4'-n-butyldiphenylether was synthesized according to a reaction represented by the following formula (4).

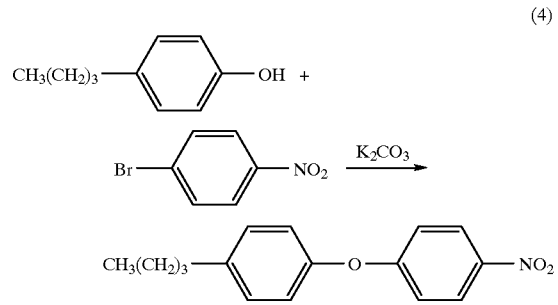

(4)

18.6 [g] of n-butylphenol, 25.0 [g] of p-bromonitrobenzene and 17.2 [g] of potassium carbonate were added to 41 [ml] of dimethylformamide, and the mixture was reacted while stirring at 140° C. for 12 hours. After cooling the reaction liquor to room temperature, it was poured into 200 [ml] of water at ambient temperature, and the mixture was extracted twice with 100 [ml] of ethyl acetate. The extraction solution (i.e. the ethyl acetate solution) was washed with water, and concentrated by evaporating off the ethyl acetate as solvent under reduced pressure. Concentration of the extraction solution was continued until there was almost no further evaporation of ethyl acetate (i.e., almost no further ethyl acetate remains in the extraction solution). The concentrated solution was then subjected to chromatography on a silica gel column using n-hexane as eluent, and a 30.2 [g] yield of 4-nitro-4'-n-butyldiphenylether was thereby obtained.

[2] Synthesis of 4-amino-4'-n-butyldiphenylether 4-amino-4'-n-butyldiphenylether was synthesized according to a reaction represented by the following formula (5).

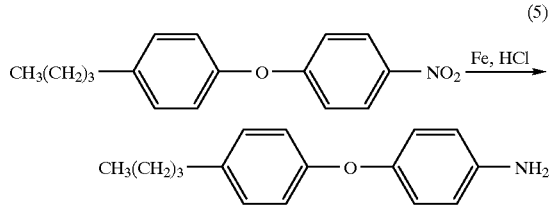

(5)

10 [ml] of concentrated hydrochloric acid (35 [wt %], ditto hereafter), 20 [g] of iron powder and 45 [ml] of water were added to 300 [ml] of dimethylformamide, the mixture was stirred at 95° C. for 1 hour, then 30.2 [g] of 4nitro-4'-n-butyldiphenylether was added, and the mixture was reacted at 95° C. while stirring for 30 min. After cooling the reaction liquor to room temperature, it was filtered using filter paper, and the filtrate was concentrated by evaporating off the dimethylformamide as solvent under reduced pressure. Concentration of the filtrate was continued until there was effectively no further evaporation of dimethylformamide (i.e., effectively no further dimethylformamide remained in the filtrate). The concentrated filtrate was poured into 200 [ml] of water, and the mixture was extracted with 200 [ml] of ethyl acetate. The extraction solution (i.e. ethyl acetate solution) was washed with water, dried, and the extraction solution was concentrated by evaporating off the ethyl acetate as solvent. Concentration of the extraction solution was continued until there was effectively no further evaporation of ethyl acetate (i.e., effectively no further ethyl acetate remains in the extraction solution). The separated crystals were filtered off using filter paper, washed with a small amount of ethyl acetate, and dried to give a 25.4 [g] yield of 4-amino-4'-n-butyldiphenylether.

[3] Synthesis of 4-diazo-4'-n-butyldiphenyletherhexafluorophosphate

Finally, 4-diazo-4'-n-butyldiphenyletherhexafluorophosphate was synthesized according to a reaction represented by the following formula (6).

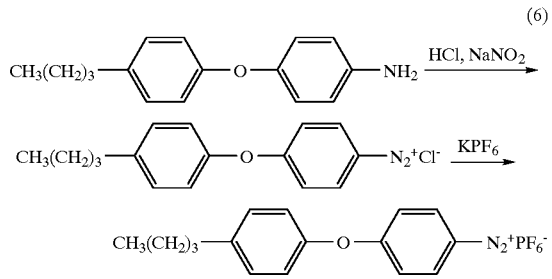

(6)

25.4 [g] of 4-amino-4'-n-butyldiphenylether was dissolved in 425 [ml] of methanol, and after dripping in 69.1 [g] of concentrated hydrochloric acid, 18.8 [g] of a 38 [wt %] aqueous solution of sodium sulphite was dripped in while cooling on ice, and a diazotization reaction was carried out by raising the temperature to 5° C. and stirring for 30 min. Next, 29.3 [g] of potassium hexafluorophosphate was added to the reaction liquor, and the mixture is stirred at 5° C. for 2 hours. The separated crystals were filtered off using filter paper, washed with water, and dried to give a 28.2 [g] yield of 4-diazo-4'-n-butyldiphenyletherhexafluorophosphate.

In this way, 4-diazo-4'-n-butyldiphenyletherhexafluorophosphate was synthesized.

Next, $^1$H-NMR measurements result of this diazonium salt will be described with reference to the following formula (7). For the $^1$H-NMR measurements, an NMR apparatus, which type is Gemini 300 manufactured by Varian, was used. To make up a sample for $^1$H-NMR measurement, 10 [mg] of the diazonium salt was dissolved in 0.5 [ml] of heavy chloroform.

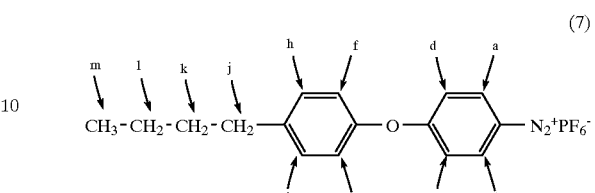

(7)

The NMR spectrum obtained shows a doublet with peak areas in a ratio of 2 centered on a chemical shift position of δ=8.41, a doublet with a peak area ratio of 2 centered on a chemical shift position of δ=7.26, a doublet with a peak area ratio of 2 centered on a chemical shift position of δ=7.16, a doublet with a peak area ratio of 2 centered on a chemical shift position of δ=7.00, a triplet with a peak area ratio of 2 centered on a chemical shift position of δ=2.64, a multiplet with a peak area ratio of 2 centered on a chemical shift position of δ=1.61, a multiplet with a peak area ratio of 2 centered on a chemical shift position of δ=1.37, and a triplet with a peak area ratio of 3 centered on a chemical shift position of δ=0.95.

These peaks are caused by protons included in 4 diazo-4'-n-butyldiphenyletherhexafluorophosphate shown in the above formula (7). The peaks centered on a chemical shift position of δ=8.41 are due to the two protons marked a and b. The peaks centered on a chemical shift position of δ=7.26 are due to the two protons marked d and e. The peaks centered on a chemical shift position of δ=7.16 are due to the two protons marked f and g. The peaks centered on a chemical shift position of δ=7.00 are due to the two protons marked h and i. The peaks centered on a chemical shift position of δ=2.64 are due to the two protons marked j. The peaks centered on a chemical shift position of δ=1.61 are due to the two protons marked k. The peaks centered on a chemical shift position of δ=1.37 are due to the two protons marked l. The peaks centered on a chemical shift position of δ=0.95 are due to the three protons marked m. This confirms that the diazonium salt which was synthesized is the desired substance, 4-diazo-4'-n-butyldiphenyletherhexafluorophosphate.

Figure 2:
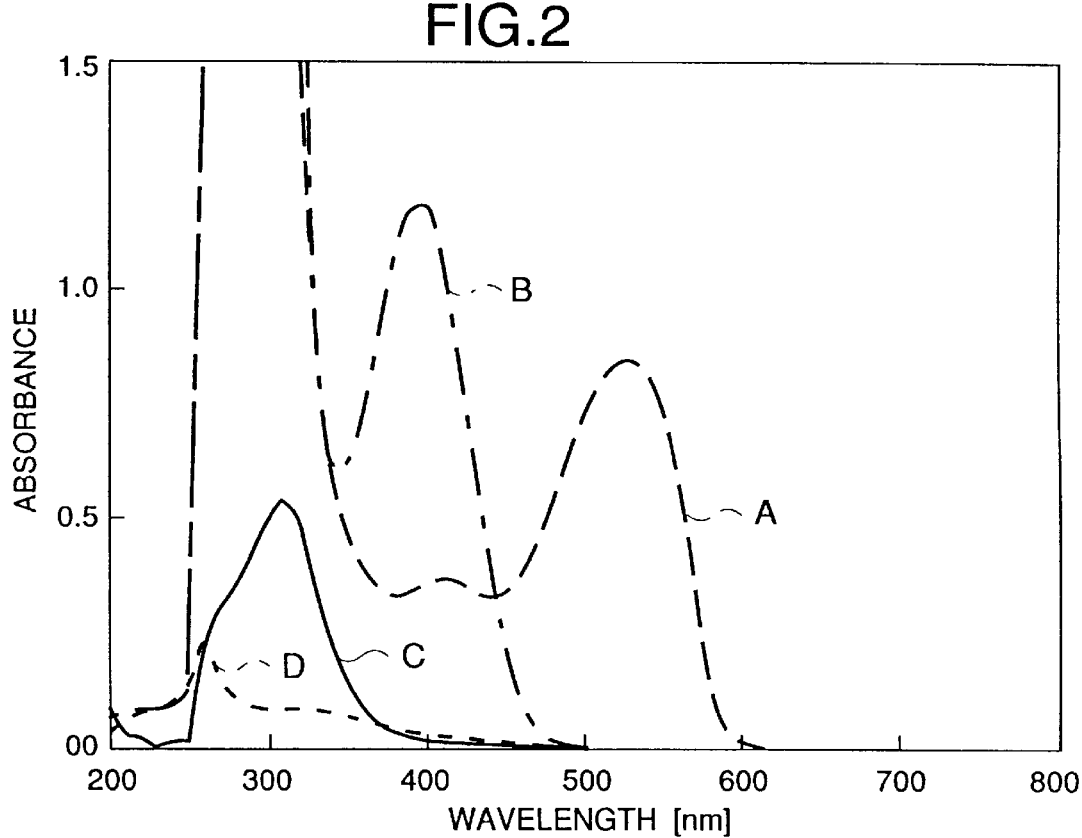
FIG. 2 is an absorption spectrum used to describe the first embodiment.

Next, the color-forming properties of 4-diazo-4'-n-butyldiphenyletherhexafluorophosphate (in some cases referred to hereafter as diazonium salt I) will be described with reference to FIG. 2. FIG. 2 is an absorption spectrum wherein the vertical axis shows optical absorption (arbitrary units) and the horizontal axis shows wavelength [nm].

After dissolving the diazonium salt I in dimethylsulfoxide, and adding naphthol AS as coupler and triphenylguanidine as basic compound to the dimethylsulfoxide solution, a magenta coloration was produced. Curve A is the absorption spectrum of the dimethylsulfoxide solution after reaction of the diazonium salt I with naphthol AS. Considering the visible wavelength region from 380 [nm] upwards, curve A shows an absorption of approximately 0.35 at wavelengths 380 [nm] and 450 [nm], and approximately 0 at a wavelength of 600 [nm].

In curve A, in the region between the wavelengths 380–450 [nm], there was a small absorption peak measuring less than 0.4 centered on a wavelength position of 410–420 [nm], and in the region between wavelengths 450–600 [nm], there was an absorption peak measuring approximately 0.85 centered on a wavelength position of 520–530 [nm].

From the fact that peaks are produced in the wavelength region 450–600 [nm], it may be understood why the dimethylsulfoxide solution after reaction exhibits a magenta coloration.

When the diazonium salt I was dissolved in dimethylsulfoxide, and naphthol AS-G as coupler and triphenylguanidine as basic compound were added to the dimethylsulfoxide solution, a yellow coloration was produced.

Curve B in FIG. 2 is the absorption spectrum of the dimethylsulfoxide solution after reaction of the diazonium salt I with naphthol AS-G. Curve B shows an absorption of approximately 0.60 at a wavelength of 350 [nm], and an absorption of approximately 0 at a wavelength of 490 [nm]. There was an absorption peak of approximately 1.2 in the wavelength region 350–490 [nm].

From the fact that a peak is produced in the wavelength region 350–490 [nm], it may be understood why the dimethylsulfoxide solution after reaction exhibits a yellow coloration.

After dissolving the diazonium salt I in dimethylsulfoxide, the dimethylsulfoxide solution was irradiated with ultraviolet light of wavelength approximately 350 [nm]. Naphthol AS and a basic compound were added to the dimethylsulfoxide solution, but no coloration was produced. Likewise, after irradiation by ultraviolet light, naphthol AS-G and a basic compound were added to the dimethylsulfoxide solution, but no coloration was produced. This is due to the fact that the diazonium salt I was decomposed by irradiating with ultraviolet light, and lost its reactivity with naphthol AS or naphthol AS-G. The curve C in FIG. 2 is the absorption spectrum of a dimethylsulfoxide solution of the diazonium salt I before irradiation by ultraviolet light, and the curve D in FIG. 2 is the absorption spectrum of a dimethylsulfoxide solution of the diazonium salt I after irradiation by ultraviolet light.

Comparing the curves C and D, it is evident that the diazonium salt I had decomposed after irradiation by ultraviolet light. In other words, whereas an absorption peak of approximately 0.5 centered on a wavelength of 300 [nm] occurs in curve C, there is no such peak in curve D.

Hence, the diazonium salt I turns a magenta color when it reacts with naphthol AS, and turns a yellow color when it reacts with naphthol AS-G. By combining naphthol AS and naphthol AS-G in a suitable proportion and using the combination as a coupler, the diazonium salt I can be made to develop a red color, a orange color, a pink color or the like (hereafter, red colors is the general term for a red color, a orange color, a pink color or the like). The 4-diazo-4'-n-butyldiphenyletherhexafluorophosphate (diazonium salt I) is therefore suitable as a diazonium salt for a thermosensitive recording medium which develops red colors. Moreover, as the diazonium salt I is decomposed by irradiating with ultraviolet light so that it loses its reactivity with naphthol AS or naphthol AS-G, an image on a thermosensitive recording medium wherein 4-diazo-4'-n-butyldiphenyletherhexafluorophosphate (diazonium salt I) is used as the diazonium salt can be fixed in this way.

Next, the results of experiments on the solubility of 4-diazo-4'-n-butyldiphenyletherhexafluorophosphate (diazonium salt I) in capsule oil will be described.

The solubility of diazonium salt I was 8 [g] per 100 [g] of dibutyl phthalate, and 12 [g] per 100 [g] of tricresyl phosphate. Considering that the solubility of 4-diazodiphenyletherhexafluorophosphate or 4-diazo-4'-methyldiphenyletherhexafluorophosphate which are conventional diazonium salts for developing red colors in 100 [g] of dibutylphthalate or 100 [g] of tricresylphosphate, is no higher than 1.0 [g], it is clear that the diazonium salt I has a high solubility in dibutyl phthalate and tricresyl phosphate.

Therefore, as the diazonium salt I of the present invention has a high solubility in dibutyl phthalate and tricresyl phosphate as capsule oils, 4-diazo-4'-n-butyldiphenyletherhexafluorophosphate (diazonium salt I) is suitable for use as a diazonium salt in a thermosensitive recording medium where the diazonium salt is sealed in microcapsules.

Next, the thermal decomposition temperature of the diazonium salt of the first embodiment was measured. Using a DTA, THERMAL ANALYZER DT-30 of Shimadzu Seisakusho, 10 [mg] of the diazonium salt of the first embodiment was heated so that the temperature rise was 10° C./min, and the exothermic peak was measured as thermal decomposition temperature. A high value of 106° C. was obtained as a result.

Second Embodiment

The diazonium salt of the second embodiment, represented by the following general formula (8), is 4-diazo-2',5'-di-n-butoxydiphenyletherhexafluorophosphate in which $R^1$ and $R^2$ are n-butyl groups, $(CH_3(CH_2)_3^-)$.

(8)

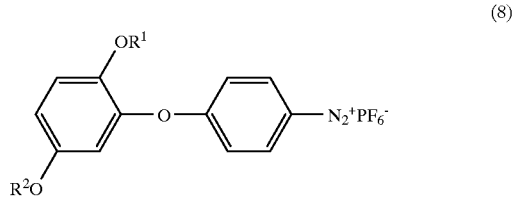

Next, a method of synthesizing the diazonium salt of this embodiment will be described.

[1] Synthesis of 1,4-di-n-butoxybenzene

First, 1,4-di-n-butoxybenzene was synthesized according to a reaction represented by the following formula (9).

(9)

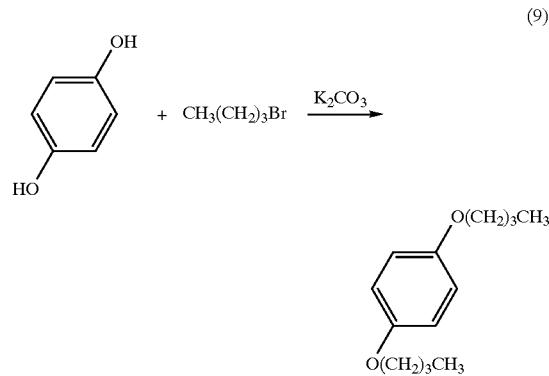

50.0 [g] of hydroquinone, 131 [g] of n-butyl bromide and 145 [g] of potassium carbonate were added to 300 [ml] of dimethylformamide, and the mixture was reacted while stirring it at 130° C. for 4 hours. After cooling the reaction liquor to room temperature, it was poured into 1500 [ml] of water at ambient temperature, and the mixture was extracted three times with 300 [ml] of ethyl acetate. The extraction solution (i.e. the ethyl acetate solution) was washed with water, and concentrated by evaporating off the ethyl acetate as solvent under reduced pressure. Concentration of the extraction solution was continued until there was almost no further evaporation of ethyl acetate (i.e., almost no further ethyl acetate remained. The concentrated solution was then subjected to chromatography on a silica gel column using n-hexane as eluent, and a 70.5 [g] yield of 1,4-di-n-butoxybenzene was thereby obtained.

[2] Synthesis of 2,5-di-n-butoxyphenol 2,5-di-n-butoxyphenol was synthesized according to a reaction represented by the following formula (10).

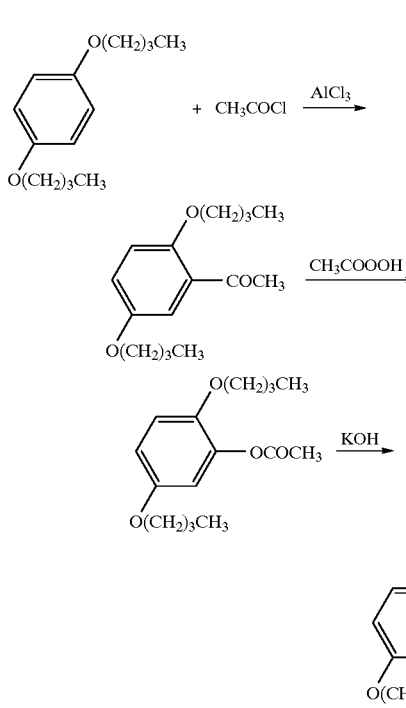

77 [ml] of acetyl chloride was added to 70.3 [g] of 1,4-di-n-butoxybenzene, 50.7 [g] of aluminum chloride was added while cooling on ice, and the reaction was carried out while stirring at −5° C. for 1 hour. The reaction liquor was poured into 1000 [ml] of water, and extracted twice with 500 [ml] methylene chloride. The extraction solution (i.e. the methylene chloride solution) was washed with water, and concentrated by evaporating off the methylene chloride as solvent under reduced pressure. Concentration of the extraction solution was continued until almost no further methylene chloride remained. The concentrated extraction solution was then subjected to chromatography on a silica gel column using a mixture of n-hexane and ethyl acetate (volume ratio of n-hexane:ethyl acetate=30:1) as eluent, and a 77.2 [g] yield of 2-acetyl-1,4-di-n-butoxybenzene was thereby obtained.

Next, 67.1 [g] of 2-acetyl-1,4-di-n-butoxybenzene was added to 54 [ml] of ethyl acetate, 83 [ml] of 40 [wt %] peracetic acid was dripped in at 40° C., and the reaction was carried out while stirring at 40° C. for 18 hours. The reaction liquor was poured into 700 [ml] of water at room temperature, and extracted twice with 300 [ml] of ethyl acetate. The extraction solvent (i.e. the ethyl acetate solution) was washed with water, and concentrated by evaporating off the ethyl acetate solvent under reduced pressure. Concentration of the extraction solution was continued until there was almost no further evaporation of ethyl acetate (i.e., almost no further ethyl acetate remained in the extraction solution). Subsequently, the separated crystals were filtered off using filter paper, washed with a small amount of ethyl acetate, and dried to obtain 53.0 [g] of 2-acetoxy-1,4-di-n-butoxybenzene.

23 [ml] of ethanol, 51.1 [g] of potassium hydroxide and 53.0 [g] of 2-acetoxy-1,4-di-n-butoxybenzene were added to 255 [ml] of water, and the mixture was reacted at 80° C. while stirring for 1 hour. After cooling the reaction liquor, it was neutralized and extracted twice with 200 [ml] of ethyl acetate. The extraction solution (i.e. the ethyl acetate solution) was washed with water, and concentrated by evaporating off the ethyl acetate as solvent under reduced pressure. Concentration of the extraction solution was continued until there was effectively no further evaporation of ethyl acetate (i.e., effectively no further ethyl acetate remained in the extraction solution). The separated crystals were filtered using filter paper, washed with a small amount of ethyl acetate, and dried to obtain 35.1 [g] of 2,5-di-n-butoxyphenol.

[3] Synthesis of 4-nitro-2',5'-di-n-butoxydiphenylether

Next, 4-nitro-2',5'-di-n-butoxydiphenylether was synthesized according to a reaction represented by the following formula (11).

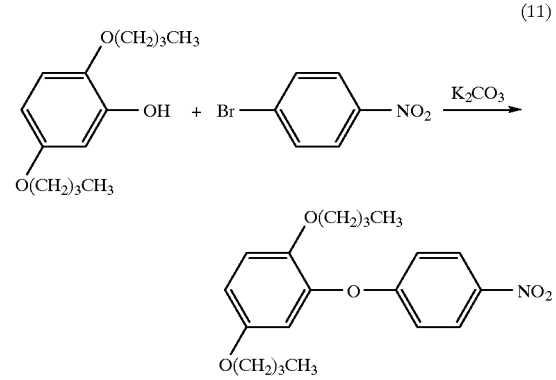

20.0 [g] of 2,5-di-n-butoxyphenyl, 17.0 [g] of p-bromonitrobenzene and 11.6 [g] of potassium carbonate were added to 28 [ml] of dimethylformamide, and the reaction was carried out while stirring at 140° C. for 12 hours. After cooling the reaction liquor to room temperature, it was poured into 1500 [ml] of water at ambient temperature, and the mixture was extracted twice with 100 [ml] of ethylacetate. The extraction solution (i.e. the ethyl acetate solution) was washed with water, and concentrated by evaporating off the ethyl acetate as solvent under reduced pressure. Concentration of the extraction solution was continued until there was almost no further evaporation of ethyl acetate (i.e., almost no further ethyl acetate remained in the extraction solution). The concentrated solution was then subjected to chromatography on a silica gel column using n-hexane as eluent, and 24.7 [g] of 4-nitro-2',5'-di-n-butoxyphenylether was thereby obtained.

[4] Synthesis of 4-amino-2',5'-di-n-butoxydiphenylether

Next, 4-amino-2',5'-di-n-butoxydiphenylether was synthesized according to a reaction represented by the following formula (12).

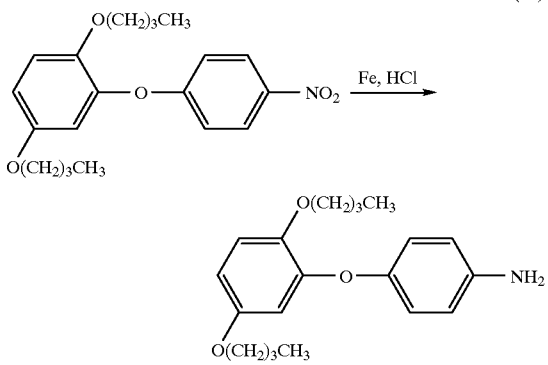

(12)

6.2 [ml] of concentrated hydrochloric acid, 12.4 [g] of iron powder and 28 [ml] of water were added to 186 [ml] of dimethylformamide, the mixture was stirred at 95° C. for 1 hour, then 24.7 [g] of 4-nitro-2',5'-di-n-butoxydiphenylether was added, and the mixture was reacted at 95° C. while stirring for 30 min. After cooling the reaction liquor to room temperature, it was filtered using filter paper, and the filtrate was concentrated by evaporating off the dimethylformamide as solvent under reduced pressure. Concentration of the filtrate was continued until there was effectively no further evaporation of dimethylformamide (i.e., effectively no further dimethylformamide remained in the extraction solution). The concentrated filtrate was poured into 200 [ml] of water, and the mixture extracted with 200 [ml] of ethyl acetate. The extraction solution (i.e. ethyl acetate solution) was washed with water, and the extraction solution concentrated by evaporating off the ethyl acetate solvent. Concentration of the extraction solution was continued until there was effectively no further evaporation of ethyl acetate (i.e., effectively no further ethyl acetate remained in the extraction solution). The concentrated solution was then subjected to chromatography on a silica gel column using a mixture of n-hexane and ethyl acetate (volume ratio of n-hexane:ethyl acetate=4:1) as eluent, and a 19.5 [g] yield of 4-amino-2',5'-di-n-butoxydiphenylether was thereby obtained.

[5] Synthesis of 4-diazo-2',5'-di-n-butoxydiphenyletherhexafluorophosphate

Finally, 4-diazo-2',5'-di-n-butoxydiphenyletherhexafluorophosphate was synthesized according to a reaction represented by the following formula (13).

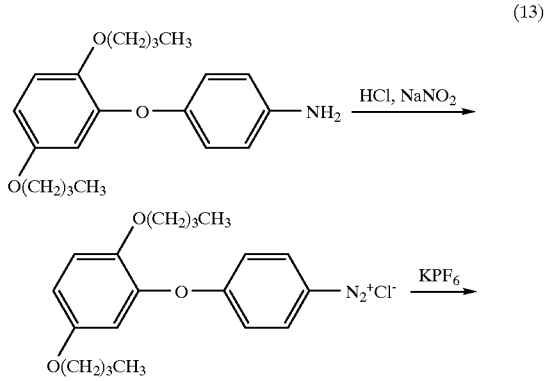

(13)

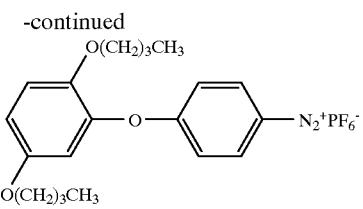

19.5 [g] of 4-amino-2',5'-di-n-butoxydiphenylether was dissolved in 240 [ml] of methanol, and after dripping in 39.0 [g] of concentrated hydrochloric acid, 10.5 [g] of a 38 [wt %] aqueous solution of sodium sulphite was dripped in while cooling on ice, and a diazotization reaction was carried out by raising the temperature to 5° C. while stirring for 30 min. Next, 16.6 [g] of potassium hexafluorophosphate was added to the reaction liquor, and the mixture was stirred at 5° C. for 2 hours. The separated crystals were filtered off using filter paper, washed with water, and dried to obtain a 15.8 [g] yield of 4-diazo-2',5'-di-n-butoxydiphenyletherhexafluorophosphate.

In this way, 4-diazo-2',5'-di-n-butoxydiphenyletherhexafluorophosphate was synthesized.

Next, $^1$H-NMR measurements of this diazonium salt will be described with reference to the following formula (14). For the $^1$H-NMR measurements, an NMR apparatus, which type is Gemini 300 manufactured by Varian, was used. To make up a sample for $^1$H-NMR measurement, 0.5 [g] of the diazonium salt was dissolved in 0.5 [ml] of heavy chloroform.

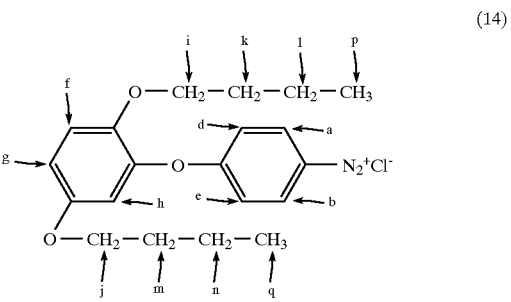

(14)

The NMR spectrum obtained shows a doublet with a peak area ratio of 2 centered on a chemical shift position of $\delta=8.28$, a doublet with a peak area ratio of 2 centered on a chemical shift position of $\delta=7.14$, a doublet with a peak area ratio of 1 centered on a chemical shift position of $\delta=6.94$, a doublet with a peak area ratio of 1 centered on a chemical shift position of $\delta=6.80$, a singlet with a peak area ratio of 1 centered on a chemical shift position of $\delta=6.71$, a multiplet with a peak area ratio of 4 centered on a chemical shift position of $\delta=3.98$, a multiplet with a peak area ratio of 2 centered on a chemical shift position of $\delta=1.77$, a multiplet with a peak area ratio of 4 centered on a chemical shift position of $\delta=1.51$, a multiplet with a peak area ratio of 2 centered on a chemical shift position of $\delta=1.17$, a triplet with a peak area ratio of 3 centered on a chemical shift position of $\delta=0.97$, and a triplet with a peak area ratio of 3 centered on a chemical shift position of $\delta=0.80$.

These peaks are caused by protons included in 4diazo-2',5'-di-n-butoxydiphenyletherhexafluorophosphate shown in the above formula (14). The peaks centered on a chemical shift position of $\delta=8.28$ are due to the two protons marked a and b. The peaks centered on a chemical shift position of $\delta=7.14$ are due to the two protons marked d and e. The peaks centered on a chemical shift position of δ=6.94 are due to the proton marked f. The peaks centered on a chemical shift position of δ=6.80 are due to the proton marked g. The peak centered on a chemical shift position of δ=6.71 is due to the proton marked h. The peaks centered on a chemical shift position of δ=3.98 are due to the four protons marked i and j. The peaks centered on a chemical shift position of δ=1.77 are due to the two protons marked k. The peaks centered on a chemical shift position of δ=1.51 are due to the four protons marked 1 and m. The peaks centered on a chemical shift position of δ=1.17 are due to the two protons marked n. The peaks centered on a chemical shift position of δ=0.97 are due to the three protons marked p. The peaks centered on a chemical shift position of δ=0.80 are due to the three protons marked q.

This confirms that the diazonium salt which was synthesized is the desired substance, 4-diazo-2',5'-d-n-butoxydiphenyletherhexafluorophosphate.

Figure 3:
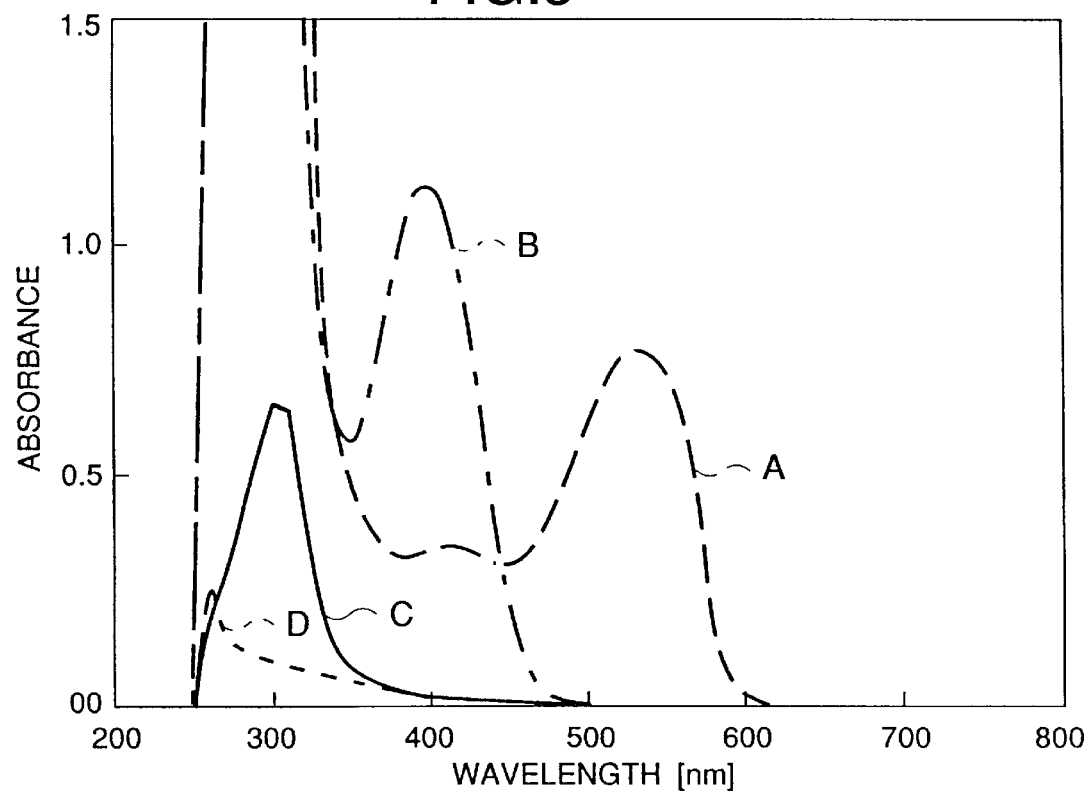
FIG. 3 is an absorption spectrum used to describe the second embodiment.

Next, the color-forming properties of 4-diazo-2',5'-di-n-butoxydiphenyletherhexafluorophosphate (in some cases referred to hereafter as diazonium salt II) will be described with reference to FIG. 3.

After dissolving the diazonium salt II in dimethylsulfoxide, and adding naphthol AS as coupler and triphenylguanidine as basic compound to the dimethylsulfoxide solution, a magenta coloration was produced. Curve A in FIG. 3 is the absorption spectrum of the dimethylsulfoxide solution after reaction of the diazonium salt I with naphthol AS. Curve A in FIG. 3 shows the same variation as that of curve A in FIG. 2 described in the case of the first embodiment. From this variation, it may be understood why the dimethylsulfoxide solution after reaction exhibits a magenta coloration.

When the diazonium salt II was dissolved in dimethylsulfoxide, and naphthol AS-G as coupler and triphenylguanidine as basic compound were added to the dimethylsulfoxide solution, a yellow coloration was produced. Curve B in FIG. 3 is the absorption spectrum of the dimethylsulfoxide solution after reaction of the diazonium salt II with naphthol AS-G. From this variation, it may be understood why the dimethylsulfoxide solution after reaction exhibits a yellow coloration.

After dissolving the diazonium salt II in dimethylsulfoxide, the dimethylsulfoxide solution was irradiated with ultraviolet light of wavelength approximately 350 [nm]. Naphthol AS and a basic compound were added to the dimethylsulfoxide solution, but no coloration was produced. Likewise, after irradiation by ultraviolet light, naphthol AS-G and a basic compound were added to the dimethylsulfoxide solution, but no coloration was produced. This is due to the fact that the diazonium salt II was decomposed by irradiating with ultraviolet light, and lost its reactivity with naphthol AS or naphthol AS-G. The curve C in FIG. 3 is the absorption spectrum of a dimethylsulfoxide solution of the diazonium salt II before irradiation by ultraviolet light, and the curve D in FIG. 3 is the absorption spectrum of a dimethylsulfoxide solution of the diazonium salt II after irradiation by ultraviolet light. Comparing the curves C and D, it is evident that the diazonium salt II had decomposed after irradiation by ultraviolet light as in the case of the first embodiment.

Hence, the diazonium salt II develops a magenta color when it reacts with naphthol AS, and develops a yellow color when it reacts with naphthol AS-G. By combining naphthol AS and naphthol AS-G in a suitable proportion and using the combination as a coupler, the diazonium salt II can be made to form red colors such as orange, red or pink. The 4-diazo-2',5'-di-n-butoxydiphenyletherhexafluorophosphate (diazonium salt II) is therefore suitable as a diazonium salt for a thermosensitive recording medium which develops a red color. Moreover, as the diazonium salt II is decomposed by irradiating with ultraviolet light so that it loses its reactivity with naphthol AS or naphthol AS-G, an image on a thermosensitive recording medium, in which 4-diazo-2', 5'-di-n-butoxydiphenyletherhexafluorophosphate (diazonium salt II) is used as the diazonium salt, can be fixed.

Next, the results of experiments on the solubility of 4-diazo-2',5'-di-n-butoxydiphenyletherhexafluorophosphate (diazonium salt II) in capsule oil will be described.

The solubility of diazonium salt II was at least 20 [g] per 100 [g] of dibutyl phthalate or per 100 [g] of tricresyl phosphate. Considering that the solubility of 4-diazodiphenyletherhexafluorophosphate in 100 [g] of dibutyl phthalate or 100 [g] of tricresyl phosphate is no higher than 0.5 [g], and the solubility of 4-diazo-4'-methyldiphenyletherhexafluorophosphate in 100 [g] of dibutyl phthalate or 100 [g] of tricresyl phosphate is no higher than 1.0 [g], it is clear that the diazonium salt II has a high solubility in dibutyl phthalate and tricresyl phosphate.

Therefore, as the diazonium salt II of the present invention has a high solubility in dibutyl phthalate and tricresyl phosphate as capsule oils, 4-diazo-2',5'-di-n-butoxydiphenyletherhexafluorophosphate (diazonium salt II) is suitable for use as a diazonium salt in a thermosensitive recording medium where the diazonium salt is sealed in microcapsules.

It will be understood that the present invention is in no way limited to the above embodiments. For example, the aforesaid embodiments were described in the case where the diazonium salt is a hexafluorophosphate (i.e. for a diazonium salt in which the complementary anion is hexafluorophosphate), however the diazonium salt may be a tetrafluoroborate (i.e. a diazonium salt in which the complementary anion is tetrafluoroborate), or a tetraphenylborate (i.e. a diazonium salt in which the complementary anion is tetraphenylborate). To synthesize a diazonium salt which is a tetrafluoroborate, potassium tetrafluoroborate or sodium tetrafluoroborate may be used instead of potassium hexafluorophosphate in the final step of the synthesis, and to synthesize a diazonium salt which is a tetraphenylborate, sodium tetraphenylborate maybe used instead of potassium hexafluorophosphate in the final step of the synthesis.

Further in the reaction with the diazonium salt, the coupler is not limited to naphthol AS to produce a magenta coloration, and is not limited to naphthol AS-G to produce a yellow coloration.

Next, the thermal decomposition temperature of the diazonium salt II of the second embodiment will be described. When exothermic peak due to thermal decomposition was measured using a DTA under the same conditions as those of the first embodiment, a value of approximately 76° C. was obtained.

Third Embodiment

The diazonium salt of the third embodiment, represented by the following general formula (15), is 4-diazo-4'-t-butyldiphenyletherhexafluorophosphate in which R is a t-butyl group.

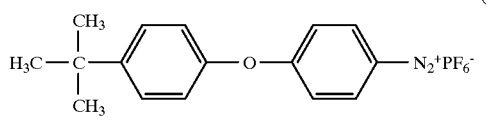
(15)

Next, a method of synthesizing the diazonium salt of this embodiment will be described.

[1] Synthesis of 4-nitro-4'-t-butyldiphenylether

First, 4-nitro-4'-t-butyldiphenylether was synthesized according to a reaction represented by the following formula (16).

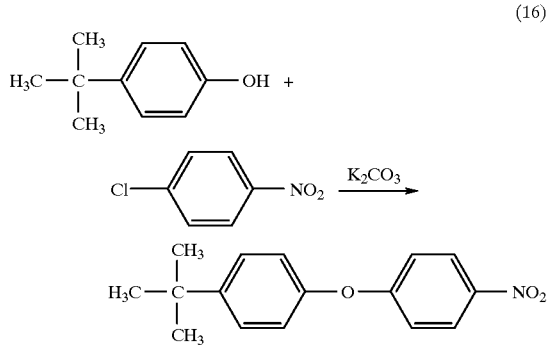
(16)

18.6 [g] of p-butyl phenol, 10.0 [g] of p-chloronitrobenzene and 10.5 [g] of potassium carbonate were added to 20 [ml] of dimethylformamide, and the mixture was reacted while stirring at 140° C. for 8 hours. After cooling the reaction liquor to room temperature, it was poured into 150 [ml] of water at ambient temperature, and the mixture was extracted with 150 [ml] of ethyl acetate. The extraction solution (i.e. the ethyl acetate solution) was washed three times with 100 [ml] of a 5 [%] aqueous solution of sodium hydroxide, washed once with 10 [%] brine, and concentrated by evaporating off the ethyl acetate as solvent under reduced pressure. Concentration of the extraction solution was continued until there was almost no further evaporation of ethyl acetate (i.e., almost no further ethyl acetate remained in the extraction solution), obtaining a 17.6 [g] yield of 4-nitro-4'-t-butyldiphenylether.

[2] Synthesis of 4-amino-4'-t-butyldiphenylether

Next, 4-amino-4'-t-butyldiphenylether was synthesized according to a reaction represented by the following formula (17).

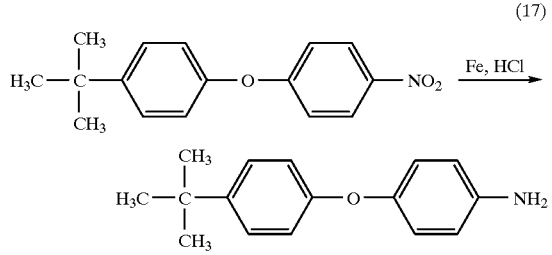
(17)

6.35 [g] of concentrated hydrochloric acid (35 [wt %] ditto hereafter), 21.7 [g] of iron powder and 72 [ml] of water were added to 90 [ml] of toluene, the mixture was stirred at 85° C. for 1 hour, then a solution of 15.0 [g] of 4-amino-4'-t-butyldiphenylether in 27 [ml] of toluene was added, and the mixture was reacted at 85° C. while stirring for 1 hour. After cooling the reaction liquor to room temperature, it was neutralized with a 20 [%] aqueous solution of sodium carbonate and filtered. The organic layer was washed with water, and the filtrate was concentrated by evaporating off the toluene as solvent under reduced pressure. Concentration of the filtrate was continued until there was effectively no further evaporation of toluene (i.e., effectively no further toluene remained in the filtrate). The separated crystals were filtered off using filter paper, and dried to give a 12.5 [g] yield of 4-amino-4'-t-butyldiphenylether.

[3] Synthesis of 4-diazo-4'-t-butyldiphenyletherhexafluorophosphate

Finally, 4-diazo-4'-t-butyldiphenyletherhexafluorophosphate was synthesized according to a reaction represented by the following formula (18).

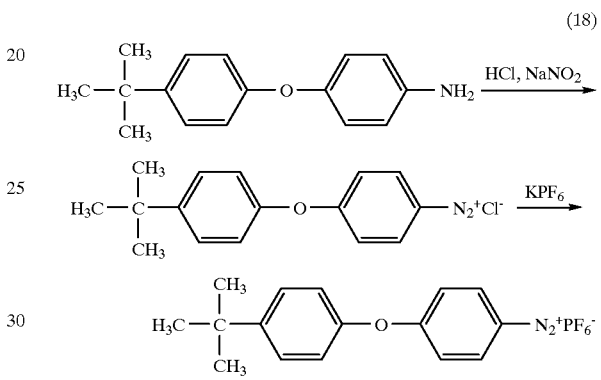
(18)

10.0 [g] of 4-amino-4'-t-butyldiphenylether and 25.9 [g] of concentrated hydrochloric acid were dissolved in 204 [ml] of water, 17 [ml] of a 20 [wt %] aqueous solution of sodium sulphite was dripped in while cooling on ice, and a diazotization reaction was carried out while stirring for 1 hour. Next, 8.43 [g] of potassium hexafluorophosphate was added to the reaction liquor, and the mixture was stirred at 2° C. for 30 min. The separated crystals were filtered off using filter paper, washed with water, and dried to give a 8.8 [g] yield of 4-diazo-4'-t-butyldiphenyletherhexafluorophosphate.

In this way, 4-diazo-4'-t-butyldiphenyletherhexafluorophosphate was synthesized, and used in the following tests.

($^1$H-NMR measurement)

First, $^1$H-NMR measurements of this diazonium salt will be described with reference to the following formula (19). For the $^1$H-NMR measurements, an NMR apparatus, which type is Gemini 300 (Model Number) manufactured by Varian, was used. To make up a sample for $^1$H-NMR measurement, 10[mg] of the diazonium salt was dissolved in 0.5 [ml] of heavy chloroform.

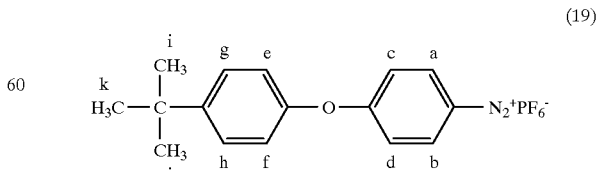
(19)

The NMR spectrum obtained shows a doublet with a peak area ratio of 2 centered on a chemical shift position of δ=8.44, a doublet with a peak area ratio of 2 centered on a chemical shift position of δ=7.50, a doublet with a peak area ratio of 1 centered on a chemical shift position of δ=7.19, a doublet with a peak area ratio of 1 centered on a chemical shift position of δ=7.03, a singlet with a peak area ratio of 9 centered on a chemical shift position of δ=1.36.

These peaks are caused by protons included in 4-diazo-4'-t-butyldiphenyletherhexafluorophosphate shown in the above formula (19). The peaks centered on a chemical shift position of δ=8.44 are due to the two protons marked a and b. The peaks centered on a chemical shift position of δ=7.50 are due to the two protons marked c and d. The peaks centered on a chemical shift position of δ=7.19 are due to the two protons marked e and f. The peaks centered on a chemical shift position of δ=7.03 are due to the two protons marked g and h. The peak centered on a chemical shift position of δ=1.36 is due to the three protons marked i, j and k.

This confirms that the diazonium salt which was synthesized is the desired substance, 4-diazo-4'-t-butyldiphenyletherhexafluorophosphate.

(Measurement of Absorption Spectrum)

Figure 4:
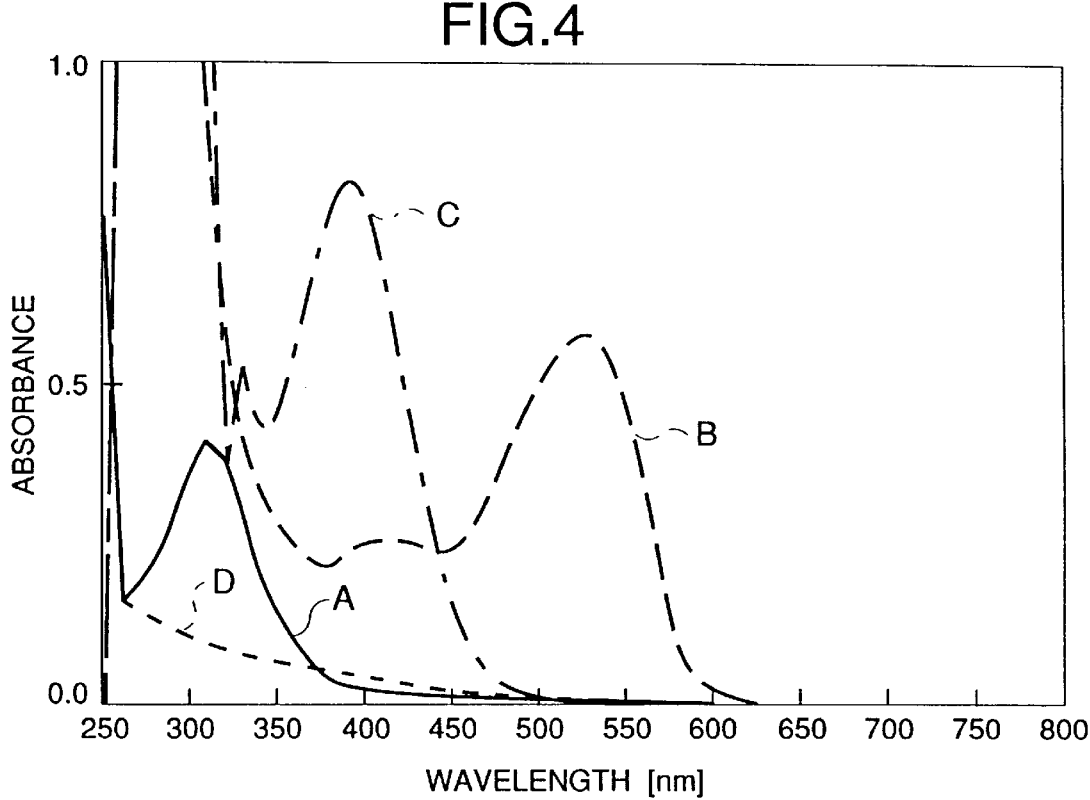
FIG. 4 is an absorption spectrum used to describe the third embodiment.

Next, the color-forming properties of 4-diazo-4'-t-butyldiphenyletherhexafluorophosphate (in some cases referred to hereafter as diazonium salt Ib) will be described with reference to FIG. 4.

After dissolving the diazonium salt Ib in dimethylsulfoxide, and adding naphthol AS as coupler and triphenylguanidine as basic compound to the dimethylsulfoxide solution, a magenta coloration was produced. Curve B in FIG. 4 is the absorption spectrum of the dimethylsulfoxide solution after reaction of the diazonium salt Ib with naphthol AS. Considering the visible wavelength region from 380 [nm] upwards, in the wavelength region 380–450 [nm], curve B shows a small absorption peak of less than 0.3 centered on the wavelengths 410–420 [nm], and in the wavelength region 450–600 [nm], curve B shows an absorption peak of approximately 0.6 centered on the wavelengths 520–530 [nm]. From the fact that the dimethylsulfoxide solution of the diazonium salt Ib of the present invention has peaks in the wavelength region 450–600 [nm], it may be understood why it exhibits a magenta coloration.

When the diazonium salt Ib was dissolved in dimethylsulfoxide, and naphthol AS-G as coupler and triphenylguanidine as basic compound were added to the dimethylsulfoxide solution, a yellow coloration was produced. Curve C in FIG. 4 is the absorption spectrum of the dimethylsulfoxide solution after reaction of the diazonium salt Ib with naphthol AS-G. In the wavelength region 350–490 [nm], curve C shows an absorption peak of approximately 0.8 centered on a wavelength of 400 [nm]. From the fact that a peak is produced in the wavelength region 350–490 [nm], it maybe understood why the dimethylsulfoxide solution after reaction exhibits a yellow coloration.

After dissolving the diazonium salt Ib in dimethylsulfoxide, the solution was irradiated with ultraviolet light of wavelength approximately 350 [nm]. Naphthol AS and a basic compound were added to the dimethylsulfoxide solution, but no coloration was produced. Likewise, after irradiation by ultraviolet light, naphthol AS-G and a basic compound were added to the dimethylsulfoxide solution, but no coloration was produced. This is due to the fact that the diazonium salt Ib was decomposed by irradiating with ultraviolet light, and lost its reactivity with naphthol AS or naphthol AS-G. The curve A in FIG. 4 is the absorption spectrum of a dimethylsulfoxide solution of the diazonium salt Ib before irradiation by ultraviolet light, and the curve D in FIG. 4 is the absorption spectrum of a dimethylsulfoxide solution of the diazonium salt Ib after irradiation by ultraviolet light. Comparing the curves A and B, it is evident that the diazonium salt Ib had decomposed after irradiation by ultraviolet light. In other words, whereas an absorption peak of approximately 0.5 centered on a wavelength of 300 [nm] occurs in curve A, there is no such peak in curve D.

Hence, the diazonium salt Ib turns a magenta color when it reacts with naphthol AS, and turns a yellow color when it reacts with naphthol AS-G. By combining naphthol AS and naphthol AS-G in a suitable proportion and using the combination as a coupler, the diazonium salt Ib can be made to form red colors such as orange, red or pink. The 4-diazo-4'-t-butyldiphenyletherhexafluorophosphate (diazonium salt Ib) is therefore suitable as a diazonium salt for a thermosensitive recording medium which forms a red color. Moreover, as the diazonium salt Ib is decomposed by irradiating with ultraviolet light so that it loses its reactivity with naphthol AS or naphthol AS-G, an image on a thermosensitive recording medium wherein 4-diazo-4'-t-butyldiphenyletherhexafluorophosphate (diazonium salt Ib) is used as the diazonium salt can be fixed in this way, and forgeries can be prevented.

(Solubility in capsule oil)

Next, the results of experiments on the solubility of 4-diazo-4'-t-butyldiphenyletherhexafluorophosphate (diazonium salt Ib) in capsule oil will be described.

The solubility of diazonium salt Ib was at least 8 [g] per 100 [g] of dibutyl phthalate and at least 8 [g] per 100 [g] of tricresyl phosphate. Considering that the solubility of 4-diazodiphenyletherhexafluorophosphate in 100 [g] of dibutylphthalate or 100 [g] of tricresyl phosphate is no higher than 0.5 [g], and the solubility of 4-diazo-4'-methyldiphenyletherhexafluorophosphate in 100 [g] of dibutyl phthalate or 100 [g] of tricresyl phosphate is no higher than 1.0 [g], it is clear that the diazonium salt Ib has a high solubility in dibutyl phthalate and tricresyl phosphate.

(Measurement of Thermal Decomposition Temperature)

Next, the thermal decomposition temperature of 4-diazo-4'-t-butyldiphenyletherhexafluorophosphate (diazonium salt Ib) was measured using the DTA under the same conditions as those of the first embodiment.

Using the DTA (Shimadzu Seisakusho, THERMAL ANALYZER DT-30), the thermal decomposition temperature of the diazonium salt Ib was found from the exothermic peak due to decomposition. As a result, only an exothermic peak due to thermal decomposition was observed without any endothermic peak due to melting, and it was situated at a high temperature of 164° C.

(Preparation and Test of Thermosensitive Recording Medium No. 1)

Finally, microcapsules were prepared using the 4diazo-4'-t-butyldiphenyletherhexafluorophosphate of the present invention (diazonium salt Ib), a thermosensitive recording medium (thermosensitive recording paper) was prepared from them, and its print properties and keeping properties were evaluated.

4 [g] of diazonium salt Ib, 48 [g] of dibutylphthalate and 48 [g] of a trimethylolpropane addition product of xylylene diisocyanate (Takenate-D110N: brand name of Takeda Yakuhin Kogyo K.K.) were blended together. 126 [g] of an 8.2 [%] aqueous solution of polyvinylalcohol was added, and the mixture was emulsified by irradiating with ultrasonic waves. The diazonium salt Ib of the present invention exhibited good solubility in the capsule oil dibutyl phthalate, and it dissolved to give a homogeneous solution in a very short time.

200 [g] of water was added, the mixture was heated while stirring at 40° C. for 4 hours, and microcapsules having an average particle diameter of 1–2 microns including walls formed from polyvinyl alcohol and isocyanate were obtained.

At the same time, 10 [g] of naphthol AS, 10 [g] of triphenylguanidine and 10 [g] of p-hydroxybenzoic acid were respectively added to 50 [g] of a 5 [%] aqueous solution of polyvinyl alcohol, and crushed and blended for 3 days using a ball mill so as to obtain a coupler dispersion, organic base dispersion and sensitizer dispersion.

30 [g] of the coupler dispersion, 30 [g] of the organic base dispersion and 60 [g] of the sensitizer dispersion were added to 100 [g] of the aforesaid microcapsules. The blended dispersion was then applied by a bar coater to paper to give a weighting of 10 [g/m²], and dried so as to obtain a thermosensitive recording medium using the diazonium salt of the present invention.

When printing was performed by a thermal printer using this thermosensitive recording paper, a magenta coloration was observed. The optical density was measured by a Macbeth densitometer using a magenta filter, and the OD was found to be a high value of 1.0 or more.

When the paper was irradiated with ultraviolet light of wavelength 350 [nm] using an ultraviolet light irradiating device, and the paper was again printed by a thermal printer, no new coloration was observed at all.

Further, when this thermosensitive recording paper was kept at room temperature under a relative humidity of 50 [%], there was no appreciable deterioration of print quality even after one year or more had elapsed.

(Preparation and Test of Thermosensitive Recording Medium No.2)

A thermosensitive recording paper using a diazonium salt of the present invention was prepared and tested in the same way as in Preparation No. 1 described above, excepting that both naphthol AS and naphthol AS-G were used instead of naphthol AS alone.

First, 10 [g] of naphthol AS, 10 [g] of naphthol AS-G, 10 [g] of triphenylguanidine and 10 [g] of p-hydroxybenzoic acid were added to 50 [g] of a 5 [%] aqueous solution of polyvinyl alcohol, and crushed and blended for 3 days using a ball mill so as to obtain a coupler dispersion, organic base dispersion and sensitizer dispersion.

24 [g] of the naphthol AS coupler dispersion, 6 [g] of the naphthol AS-G coupler dispersion, 30 [g] of the organic base dispersion and 60 [g] of the sensitizer dispersion were blended with and dispersed in 100 [g] of the microcapsules prepared in the third embodiment. The blended dispersion was then applied by a bar coater to paper to give a weighting of 10 [g/m²], and dried so as to obtain a thermosensitive recording medium using the diazonium salt of the present invention.

When printing was performed by a thermal printer using this thermosensitive recording paper, a red coloration was observed. The optical density was measured by a Macbeth densitometer using a magenta filter, and the OD was found to be a high value of 1.0 or more.

When the paper was irradiated with ultraviolet light of wavelength 350 [nm] using an ultraviolet light irradiating device, and the paper was again printed by a thermal printer, no new coloration was observed at all.

Further, when this thermosensitive recording paper was kept at room temperature under a relative humidity of 50 [%], there was no appreciable deterioration of print quality even after one year or more had elapsed.

Fourth Embodiment

The diazonium salt of the fourth embodiment, represented by the following general formula (20), is 4-diazo-4'-sec-butyldiphenyletherhexafluorophosphate in which R is a sec-butyl group.

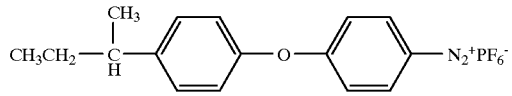

(20)

Next, a method of synthesizing the diazonium salt of this embodiment will be described.

[1] Synthesis of 4-nitro-4'-sec-butyldiphenylether

First, 4-nitro-4'-sec-butyldiphenylether was synthesized according to a reaction represented by the following formula (21).

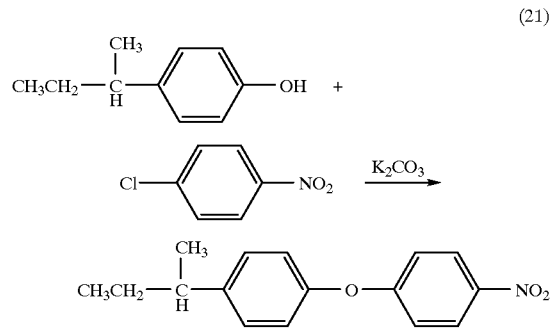

(21)

10.1 [g] of p-butyl phenol, 10.0 [g] of p-chloronitrobenzene and 10.5 [g] of potassium carbonate were added to 20 [ml] of dimethylformamide, and the mixture was reacted while stirring at 140° C. for 6 hours. After cooling the reaction liquor to room temperature, it was poured into 150 [ml] of water at ambient temperature, and the mixture was extracted with 150 [ml] of ethyl acetate. The extraction solution (i.e., the ethyl acetate solution) was washed three times with 100 [ml] of a 5 [%] aqueous solution of sodium hydroxide, washed once with 10 [%] brine, and concentrated by evaporating off the ethyl acetate solvent under reduced pressure. Concentration of the extraction solution was continued until there is almost no further evaporation of ethyl acetate (i.e., almost no further ethyl acetate remained in the extraction solution), giving a 17.6 [g] yield of 4-nitro-4'-sec-butyldiphenylether.

[2] Synthesis of 4-amino-4'-sec-butyldiphenylether

Next, 4-amino-4'-sec-butyldiphenylether was synthesized according to a reaction represented by the following formula (22).

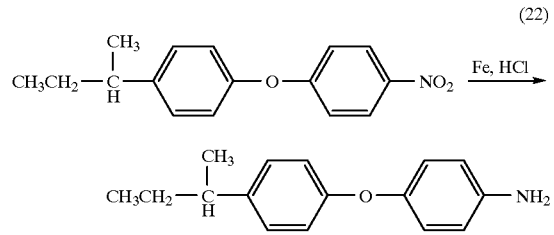

(22)

6.35 [g] of concentrated hydrochloric acid (35 [wt %]—ditto hereafter), 21.7 [g] of iron powder and 72 [ml] of water were added to 90 [ml] of toluene, the mixture was stirred at 85° C. for 1 hour, then a solution of 15.0 [g] of 4-amino-4'-sec-butyldiphenylether in 27 [ml] of toluene was added, and the mixture was reacted at 85° C. while stirring for 1 hour. After cooling the reaction liquor to room temperature, it was neutralized with a 20 [%] aqueous solution of sodium carbonate and filtered. The organic layer was washed with water, and the filtrate was concentrated by evaporating off the toluene as solvent under reduced pressure. Concentration of the filtrate was continued until there is effectively no further evaporation of toluene (i.e., effectively no further toluene remained in the filtrate). The separated crystals were filtered off using filter paper, and dried to give a 13.0 [g] yield of 4-amino-4'-sec-butyldiphenylether.

[3] Synthesis of 4-diazo-4'-sec-butyldiphenyletherhexafluorophosphate

Finally, 4-diazo-4'-sec-butyldiphenyletherhexafluorophosphate was synthesized according to a reaction represented by the following formula (23).

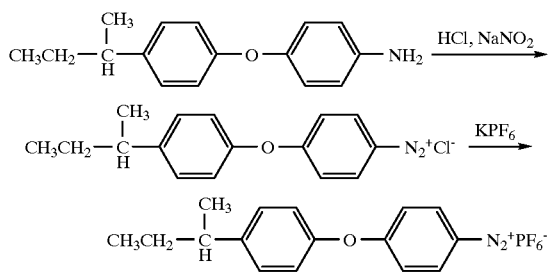

(23)

10.0 [g] of 4-amino-4'-sec-butyldiphenylether and 25.9 [g] of concentrated hydrochloric acid were dissolved in 204 [ml] of water, 17 [ml] of a 20 [wt %] aqueous solution of sodium sulphite was dripped in while cooling on ice, and a diazotization reaction was carried out while stirring for 1.5 hours. Next, 8.43 [g] of potassium hexafluorophosphate was added to the reaction liquor, and the mixture was stirred at 2° C. for 30 min. The separated crystals were filtered off using filter paper, washed with water, and dried to give a 10.0 [g] yield of 4-diazo-4'-sec-butyldiphenyletherhexafluorophosphate.

In this way, 4-diazo-4'-sec-butyldiphenyletherhexafluorophosphate was synthesized, and used in the following tests.

($^1$H-NMR measurement)

First, $^1$H-NMR measurements of this diazonium salt will be described with reference to the following formula (24). $^1$H-NMR measurements were carried out in the same way as in the first embodiment.

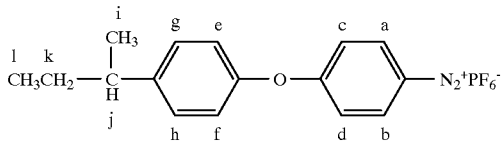

(24)

The NMR spectrum obtained shows a doublet with a peak area ratio of 2 centered on a chemical shift position of δ=8.43, a doublet with a peak area ratio of 2 centered on a chemical shift position of δ=7.29, a doublet with a peak area ratio of 1 centered on a chemical shift position of δ=7.18, a doublet with a peak area ratio of 1 centered on a chemical shift position of δ=7.03, a multiplet with a peak area ratio of 1 centered on a chemical shift position of δ=2.65, a multiplet with a peak area ratio of 2 centered on a chemical shift position of δ=1.61, a doublet with a peak area ratio of 3 centered on a chemical shift position of δ=1.27, and a triplet with a peak area ratio of 3 centered on a chemical shift position of δ=0.86.

These peaks are caused by protons included in 4-diazo-4'-sec-butyldiphenyletherhexafluorophosphate shown in the above formula (24). The peaks centered on a chemical shift position of δ=8.43 are due to the two protons marked a and b. The peaks centered on a chemical shift position of δ=7.29 are due to the two protons marked c and d. The peaks centered on a chemical shift position of δ=7.18 are due to the two protons marked e and f. The peaks centered on a chemical shift position of δ=7.03 are due to the two protons marked g and h. The peaks centered on a chemical shift position of δ=2.65 are due to the proton marked j. The peaks centered on a chemical shift position of δ=1.61 are due to the two protons marked k. The peaks centered on a chemical shift position of δ=1.27 are due to the three protons marked i. The peaks centered on a chemical shift position of δ=0.86 are due to the three protons marked 1.

This confirms that the diazonium salt which was synthesized is the desired substance, 4-diazo-4'-sec-butyldiphenyletherhexafluorophosphate (in some cases referred to hereafter as diazonium salt Ic).

(Measurement of Absorption Spectrum)

Figure 5:
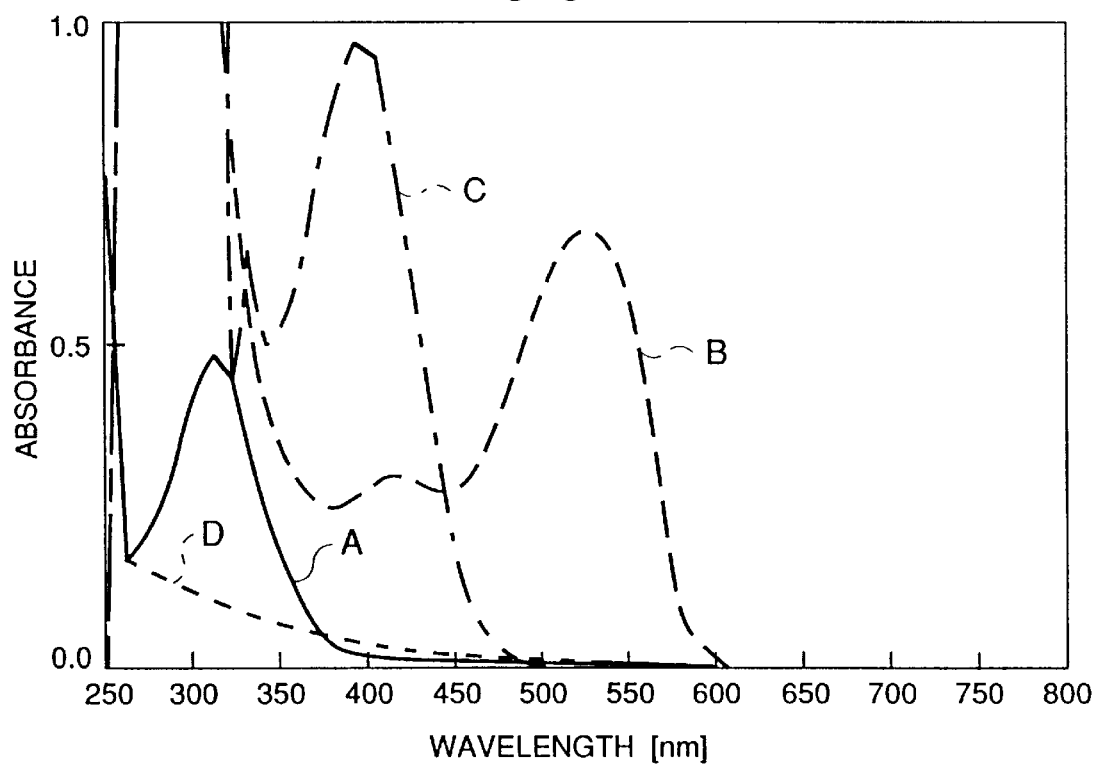
FIG. 5 is an absorption spectrum used to describe the fourth embodiment.

Next, the color-forming properties of diazonium salt Ic will be described with reference to FIG. 5. FIG. 5 is an absorption spectrum wherein the vertical axis shows optical absorption (arbitrary units) and the horizontal axis shows wavelength [nm].

After dissolving the diazonium salt Ic in dimethylsulfoxide, and adding naphthol AS as coupler and triphenylguanidine as basic compound to the dimethylsulfoxide solution, a magenta coloration was produced. Curve B in FIG. 5 is the absorption spectrum of the dimethylsulfoxide solution after reaction of the diazonium salt Ic with naphthol AS. This curve B shows the same variation as that of curve B in FIG. 4 described in the case of the third embodiment. From the fact that the dimethylsulfoxide solution of the diazonium salt Ic of the present invention has peaks in the wavelength region 450–600 [nm], it may be understood why it exhibits a magenta coloration.

When the diazonium salt Ic was dissolved in dimethylsulfoxide, and naphthol AS-G as coupler and triphenylguanidine as basic compound were added to the dimethylsulfoxide solution, a yellow coloration was produced. Curve C in FIG. 5 is the absorption spectrum of the dimethylsulfoxide solution after reaction of the diazonium salt Ib with naphthol AS-G. This curve C shows the same variation as that of curve C in FIG. 4 described in the case of the third embodiment. From the fact that the dimethylsulfoxide solution of the diazonium salt Ic of the present invention has peaks in the wavelength region 450–600 [nm], it may be understood why it exhibits a yellow coloration.

After dissolving the diazonium salt Ic in dimethylsulfoxide, the solution was irradiated with ultraviolet light of wavelength approximately 350 [nm]. Naphthol AS and a basic compound were added to the dimethylsulfoxide solution, but no coloration was produced. Likewise, after irradiation by ultraviolet light, naphthol AS-G and a basic compound were added to the dimethylsulfoxide solution, but no coloration was produced. This is due to the fact that the diazonium salt Ic was decomposed by irradiating with ultraviolet light, and lost its reactivity with naphthol AS or naphthol AS-G. The curve A in FIG. 5 is the absorption spectrum of a dimethylsulfoxide solution of the diazonium salt Ic before irradiation by ultraviolet light, and the curve D in FIG. 5 is the absorption spectrum of a dimethylsulfoxide solution of the diazonium salt Ic after irradiation by ultraviolet light. Comparing the curves A and D, it is evident that the diazonium salt Ic had decomposed after irradiation by ultraviolet light as in the case of the third embodiment.

Hence, the diazonium salt Ic turns a magenta color when it reacts with naphthol AS, and turns a yellow color when it reacts with naphthol AS-G. By combining naphthol AS and naphthol AS-G in a suitable proportion and using the combination as a coupler, the diazonium salt Ic can be made to form red colors such as orange, red or pink. The 4-diazo-4'-sec-butyldiphenyletherhexafluorophosphate (diazonium salt Ic) is therefore suitable as a diazonium salt for a thermosensitive recording medium which forms a red color. Moreover, as the diazonium salt Ic is decomposed by irradiating with ultraviolet light so that it loses its reactivity with naphthol AS or naphthol AS-G, an image on a thermosensitive recording medium using the diazonium salt Ic can be fixed in this way, and forgeries can be prevented.

(Solubility of Capsule Oil)

Next, the results of experiments on the solubility of 4-diazo-4'-sec-butyldiphenyletherhexafluorophosphate (diazonium salt Ic) in capsule oil will be described.

The solubility of diazonium salt Ic was at least 10 [g] per 100 [g] of dibutyl phthalate and at least 10 [g] per 100 [g] of tricresyl phosphate. Hence, the diazonium salt Ic dissolves easily in capsule oil within a short time to give a homogeneous solution, thus confirming the suitability of the diazonium salt of the present invention for a thermosensitive recording medium using microcapsules.

(Measurement of Thermal Decomposition Temperature)

Next, the thermal decomposition temperature of 4diazo-4'-sec-butyldiphenyletherhexafluorophosphate (diazonium salt Ic) was measured under the same conditions as those of the first embodiment. As a result, an endothermic peak due to melting and an exothermic peak due to thermal decomposition were observed, the exothermic peak being situated at a high decomposition temperature of 117° C.

(Preparation and Test of Thermosensitive Recording Medium No. 1)

Microcapsules were prepared using the 4-diazo-4'-sec-butyldiphenyletherhexafluorophosphate of the present invention (diazonium salt Ic) in the same way as in the third embodiment, a thermosensitive recording medium (thermosensitive recording paper) was prepared from them, and its print properties and keeping properties were evaluated.

When printing was performed by a thermal printer using this thermosensitive recording paper, a magenta coloration was observed. The optical density was measured by a Macbeth densitometer using a magenta filter, and the OD was found to be a high value of 1.0 or more.

When the paper was irradiated with ultraviolet light of wavelength 350 [nm] using an ultraviolet light irradiating device, and the paper was again printed by a thermal printer, no new coloration was observed at all.

Further, when this thermosensitive recording paper was kept at room temperature under a relative humidity of 50 [%], there was no appreciable deterioration of print quality even after one year or more had elapsed.

(Preparation and Test of Thermosensitive Recording Medium No.2)

A thermosensitive recording paper using a diazonium salt of the present invention was prepared and tested in the same way as in Preparation No. 1 described above, excepting that naphthol AS-G was used as coupler instead of naphthol AS.

When printing was performed by a thermal printer using this thermosensitive recording paper, a red coloration was observed. The optical density was measured by a Macbeth densitometer using a magenta filter, and the OD was found to be a high value of 1.0 or more.

When the paper was irradiated with ultraviolet light of wavelength 350 [nm] using an ultraviolet light irradiating device, and the paper was again printed by a thermal printer, no new coloration was observed at all.

Further, when this thermosensitive recording paper was kept at room temperature under a relative humidity of 50 [%], there was no appreciable deterioration of print quality even after one year or more had elapsed.

The first and second diazonium salts according to the present invention therefore have the following advantages.

[1] They form a magenta coloration with a coupler such as naphthol AS, form a yellow coloration with a coupler such as naphthol AS-G, and give a high optical density.

[2] They not only form single colors, but when used in conjunction with naphthol AS and naphthol AS-G combined in a suitable proportion, they can form any kind of red coloration such as orange, red or pink.

[3] They are easily decomposed by irradiating with ultraviolet light of a predetermined wavelength, and therefore instantaneously lose their reactivity with a coupler. They therefore allow easy, rapid fixing of an image on a thermosensitive recording medium. It was moreover confirmed that this characteristic could be used to prevent forgeries on the thermosensitive recording medium.

[4] A high solubility was obtained in capsule oils such as for example dibutyl phthalate or tricresyl phosphate. Specifically, whereas the solubility of conventional diazonium salts was of the order of less than 1 [g] per 100 [g] of capsule oil, the diazonium salt of the present invention exhibits a solubility of 1 [g] or higher, and preferably a higher value in the range 3–30 [g] per 100 [g] of capsule oil. The first and second diazonium salts of the present invention may therefore easily be dissolved in capsule oil to give homogeneous solutions, and may thus be sealed inside microcapsules. As a result, a thermosensitive recording medium was obtained which forms high density, high contrast images.

[5] As they have a suitable thermal decomposition temperature, they provide a thermosensitive recording medium which, when exposed to heat using a thermal head or the like, not only allows high density, high contrast images to be obtained, but also has good keeping properties at room temperature before exposure to heat.

[6] In the synthesis of the first diazonium salt according to the present invention, low-cost p-t-butylphenol or p-sec-butylphenol may be used. This provides more economical and highly heat-resistant diazonium salts.

What is claimed is:

1. A diazonium salt for a color-forming layer of a thermosensitive recording medium, having formula (1):

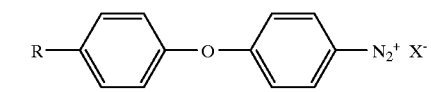

(1)

wherein R is an alkyl group having four carbon atoms which is selected from the group consisting of n-butyl, t-butyl, and sec-butyl, and $X^-$ is selected from the group tetraphenylborate ion $(C_6H_5)_4B^-$.

2. A thermosensitive recording medium comprising a color-forming layer which includes a diazonium salt, a basic compound and a coupler:

said diazonium salt having formula (1):

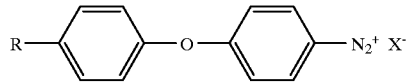

(1)

wherein R is an alkyl group having four carbon atoms which is selected from the group consisting of n-butyl, t-butyl, and sec-butyl, and $X^-$ is selected from the group consisting of hexafluorophosphate ion $PF_6^-$, tetrafluoroborate ion $BF_4^-$ and tetraphenylborate ion $(C_6H_5)_4B^-$.

3. A thermosensitive recording medium, comprising a color-forming layer which includes:

a diazonium salt, a basic compound, and a coupler, wherein the diazonium salt has a formula (2):

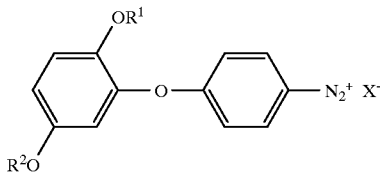

(2)

wherein $R^1$ and $R^2$ are alkyl groups each having one or more carbon atoms, and $X^-$ is selected from the group consisting of hexafluorophosphate ion $PF_6^-$, tetrafluoroborate ion $BF_4^-$ and tetraphenylborate ion $(C_6H_5)_4B^-$.

4. The thermosensitive recording medium of claim 3, wherein at least one of $R^1$ and $R^2$ in the formula (2) is an alkyl group having three to eight carbon atoms.

5. The thermosensitive recording medium of claim 3, wherein at least 1 gram of the diazonium salt is dissolvable per 100 gram of capsule oil.

6. The thermosensitive recording medium of claim 3, wherein the diazonium salt is decomposed by irradiating ultraviolet light of wavelength 250–380 nm.

7. The thermosensitive recording medium of claim 3, wherein the diazonium salt has a thermal decomposition exothermic peak temperature which is at least 70° C. when the diazonium salt is heated so as to rise in temperature at a rate of 10° C./min.

8. A thermosensitive recording medium of claim 3, wherein the diazonium salt is sealed in a microcapsule together with capsule oil, and is separated from the basic compound and coupler by a partition of the microcapsule.

* * * * *

UNITED STATES PATENT AND TRADEMARK OFFICE
CERTIFICATE OF CORRECTION

PATENT NO.   : 5,935,756
DATED        : August 10, 1999
INVENTOR(S)  : Katsuaki Kaifu et al.

Page 1 of 1

It is certified that error appears in the above-identified patent and that said Letters Patent is hereby corrected as shown below:

Claim 1,
The second line from the end, before "tetraphenylborate ion $(C_6H_5)_4B^-$", insert
-- consisting of hexafluorophosphate ion $PF_6^-$ tetrafluoroborate ion $BF_4^-$ and --.

Signed and Sealed this

Fifteenth Day of January, 2002

Attest:

Attesting Officer

JAMES E. ROGAN
Director of the United States Patent and Trademark Office